(12) United States Patent
Gartstein et al.

(10) Patent No.: US 7,108,681 B2
(45) Date of Patent: Sep. 19, 2006

(54) MICROSTRUCTURES FOR DELIVERING A COMPOSITION CUTANEOUSLY TO SKIN

(75) Inventors: Vladimir Gartstein, Cincinnati, OH (US); Faiz Feisal Sherman, West Chester, OH (US)

(73) Assignee: Corium International, Inc., Redwood City, CA (US)

( * ) Notice: Subject to any disclaimer, the term of this patent is extended or adjusted under 35 U.S.C. 154(b) by 252 days.

(21) Appl. No.: 09/952,391

(22) Filed: Sep. 14, 2001

(65) Prior Publication Data

US 2002/0045859 A1    Apr. 18, 2002

Related U.S. Application Data

(60) Provisional application No. 60/240,730, filed on Oct. 16, 2000, provisional application No. 60/240,787, filed on Oct. 16, 2000.

(51) Int. Cl.
*A61M 5/00* (2006.01)
(52) U.S. Cl. .................. 604/173; 606/167; 604/500; 604/556; 604/573
(58) Field of Classification Search ............... 606/131, 606/201, 204, 204.35; 604/20, 22, 272–274, 604/500, 501, 19, 46–47; 602/45, 48–51, 602/54, 56, 58
See application file for complete search history.

(56) References Cited

U.S. PATENT DOCUMENTS

| | | | |
|---|---|---|---|
| 3,918,449 A | | 11/1975 | Pistor |
| 3,964,482 A | * | 6/1976 | Gerstel et al. ........... 604/890.1 |
| 4,055,029 A | | 10/1977 | Kalbow |
| 4,180,232 A | | 12/1979 | Hardigg |
| 4,381,963 A | | 5/1983 | Goldstein et al. |
| 4,585,991 A | | 4/1986 | Reid et al. |
| 4,630,603 A | * | 12/1986 | Greenway .................. 602/45 |
| 4,784,737 A | | 11/1988 | Ray et al. |
| 4,837,049 A | | 6/1989 | Byers et al. |
| 5,134,079 A | | 7/1992 | Cusack et al. |
| 5,156,591 A | | 10/1992 | Gross et al. |
| 5,158,073 A | * | 10/1992 | Bukowski .................. 601/28 |

(Continued)

FOREIGN PATENT DOCUMENTS

DE          2319591          11/1974

(Continued)

OTHER PUBLICATIONS

McAllister, H., "Micromachined Microneedles for Transdermal Drug Delivery", Allen & Prausnitz, Georgia Institute of Technology, Atlanta, GA.

(Continued)

*Primary Examiner*—Julian W. Woo
*Assistant Examiner*—Nguyen Victor
(74) *Attorney, Agent, or Firm*—Reed Intellectual Property Law Group

(57) ABSTRACT

An improved method and apparatus is provided as a system to deliver a composition, preferably a medical or pharmaceutical composition or active, through the stratum corneum of skin, without introducing bleeding or damage to tissue, and absent pain or other trauma. The dimensions and shapes of the microelements are controlled so as to control the penetration depth into the skin. The microelements can be "hollow" such that passageways are created therethrough to allow the composition to flow from a chamber, through the microelements, and into the skin. Alternatively, the microelements can be "solid," and the composition is applied directly to the skin just before or just after the microelements are applied to the skin surface to create the openings in the stratum corneum.

16 Claims, 18 Drawing Sheets

U.S. PATENT DOCUMENTS

| | | | |
|---|---|---|---|
| 5,162,043 A | 11/1992 | Lew et al. | |
| 5,198,192 A | 3/1993 | Saito et al. | |
| 5,215,088 A | 6/1993 | Normann et al. | |
| 5,250,023 A | 10/1993 | Lee et al. | |
| 5,250,067 A * | 10/1993 | Gelfer et al. | 606/189 |
| 5,256,360 A | 10/1993 | Li | |
| 5,279,544 A | 1/1994 | Gross et al. | |
| 5,318,557 A | 6/1994 | Gross | |
| 5,320,600 A | 6/1994 | Lambert | |
| 5,362,307 A | 11/1994 | Guy et al. | |
| 5,383,512 A | 1/1995 | Jarvis | |
| 5,487,726 A | 1/1996 | Rabineau et al. | |
| 5,498,235 A | 3/1996 | Flower | |
| 5,512,219 A * | 4/1996 | Rowland et al. | 264/1.6 |
| 5,527,288 A | 6/1996 | Gross et al. | |
| 5,531,675 A | 7/1996 | Yoo | |
| 5,536,263 A * | 7/1996 | Rolf et al. | 604/307 |
| 5,551,953 A | 9/1996 | Lattin et al. | |
| 5,567,376 A | 10/1996 | Turi et al. | |
| 5,591,123 A | 1/1997 | Sibalis et al. | |
| 5,591,139 A | 1/1997 | Lin et al. | |
| 5,611,806 A * | 3/1997 | Jang | 606/167 |
| 5,645,977 A | 7/1997 | Wu et al. | |
| 5,658,515 A | 8/1997 | Lee et al. | |
| 5,676,850 A | 10/1997 | Reed et al. | |
| 5,681,580 A | 10/1997 | Jang et al. | |
| 5,697,901 A | 12/1997 | Ericksson | |
| 5,704,520 A | 1/1998 | Gross | |
| 5,711,761 A | 1/1998 | Untereker et al. | |
| 5,728,089 A * | 3/1998 | Lal et al. | 606/1 |
| 5,730,714 A | 3/1998 | Guy et al. | |
| 5,735,273 A | 4/1998 | Kurnik et al. | |
| 5,771,890 A | 6/1998 | Tamada | |
| 5,800,420 A | 9/1998 | Gross et al. | |
| 5,807,375 A | 9/1998 | Gross et al. | |
| 5,814,020 A | 9/1998 | Gross | |
| 5,820,622 A | 10/1998 | Gross et al. | |
| 5,827,183 A | 10/1998 | Kurnik et al. | |
| 5,848,985 A | 12/1998 | Muroki | |
| 5,848,990 A | 12/1998 | Cirelli et al. | |
| 5,848,991 A | 12/1998 | Gross et al. | |
| 5,855,801 A | 1/1999 | Lin et al. | |
| 5,873,849 A | 2/1999 | Bernard | |
| 5,879,326 A * | 3/1999 | Godshall et al. | 604/506 |
| 5,938,684 A * | 8/1999 | Lynch et al. | 606/204 |
| 5,948,488 A | 9/1999 | Marecki et al. | |
| 5,964,729 A | 10/1999 | Choi et al. | |
| 5,983,136 A | 11/1999 | Kamen | |
| 6,014,584 A | 1/2000 | Hofmann et al. | |
| 6,023,629 A | 2/2000 | Tamada | |
| 6,024,553 A | 2/2000 | Shimalla | |
| 6,036,659 A | 3/2000 | Ray et al. | |
| 6,038,465 A | 3/2000 | Melton, Jr. | |
| 6,047,208 A | 4/2000 | Flower | |
| 6,050,988 A | 4/2000 | Zuck | |
| 6,055,453 A | 4/2000 | Hofmann et al. | |
| 6,083,196 A | 7/2000 | Trautman et al. | |
| 6,091,975 A | 7/2000 | Daddona et al. | |
| 6,106,751 A | 8/2000 | Talbot et al. | |
| 6,129,696 A | 10/2000 | Sibalis | |
| 6,132,755 A * | 10/2000 | Eicher et al. | 424/427 |
| 6,135,990 A | 10/2000 | Heller et al. | |
| 6,183,434 B1 | 2/2001 | Eppstein | |
| 6,216,034 B1 | 4/2001 | Hofmann et al. | |
| 6,219,574 B1 | 4/2001 | Cormier et al. | |
| 6,230,051 B1 | 5/2001 | Cormier et al. | |
| 6,241,701 B1 | 6/2001 | Hofmann | |
| 6,256,533 B1 | 7/2001 | Yuzhakov et al. | |
| 6,312,612 B1 | 11/2001 | Sherman et al. | |
| 6,322,808 B1 | 11/2001 | Trautman et al. | |
| 6,334,856 B1 * | 1/2002 | Allen et al. | 604/191 |
| 6,355,054 B1 | 3/2002 | Neuberger | |
| 6,375,627 B1 | 4/2002 | Mauze et al. | |
| 6,379,324 B1 * | 4/2002 | Gartstein et al. | 604/22 |
| 6,440,096 B1 | 8/2002 | Lastovich et al. | |
| 6,451,240 B1 | 9/2002 | Sherman et al. | |
| 6,471,903 B1 | 10/2002 | Sherman et al. | |
| 6,476,288 B1 | 11/2002 | VanRijswijck et al. | |
| 6,494,830 B1 | 12/2002 | Wessel | |
| 6,503,231 B1 | 1/2003 | Prausnitz et al. | |
| 6,511,463 B1 | 1/2003 | Wood et al. | |
| 6,532,386 B1 | 3/2003 | Sun et al. | |
| 6,533,884 B1 * | 3/2003 | Mallik | 156/209 |
| 6,537,242 B1 | 3/2003 | Palmer | |
| 6,558,361 B1 | 5/2003 | Yeshurun | |
| 6,562,014 B1 | 5/2003 | Lin et al. | |
| 6,565,532 B1 | 5/2003 | Yuzhakov et al. | |
| 6,591,124 B1 | 7/2003 | Sherman et al. | |
| 6,591,133 B1 | 7/2003 | Joshi | |
| 6,611,706 B1 | 8/2003 | Avrahami et al. | |
| 6,611,707 B1 * | 8/2003 | Prausnitz et al. | 604/21 |
| 6,623,457 B1 | 9/2003 | Rosenberg | |
| 6,629,949 B1 | 10/2003 | Douglas | |
| 6,689,103 B1 | 2/2004 | Palasis | |
| 6,743,211 B1 | 6/2004 | Prausnitz et al. | |
| 6,767,341 B1 | 7/2004 | Cho | |
| 6,770,480 B1 | 8/2004 | Canham | |
| 6,778,853 B1 | 8/2004 | Heller et al. | |
| 6,835,184 B1 | 12/2004 | Sage et al. | |
| 6,881,203 B1 | 4/2005 | Delmore et al. | |
| 2001/0023324 A1 | 9/2001 | Pronovost et al. | |
| 2002/0006355 A1 | 1/2002 | Whitson | |
| 2002/0032415 A1 | 3/2002 | Trautman et al. | |
| 2002/0045859 A1 | 4/2002 | Gartstein et al. | |
| 2002/0045907 A1 | 4/2002 | Sherman et al. | |
| 2002/0133129 A1 | 9/2002 | Arias et al. | |
| 2002/0138049 A1 | 9/2002 | Allen et al. | |
| 2002/0177858 A1 | 11/2002 | Sherman et al. | |
| 2003/0199812 A1 | 10/2003 | Rosenberg | |
| 2003/0208138 A1 | 11/2003 | Olson | |
| 2003/0208167 A1 | 11/2003 | Prausnitz et al. | |
| 2003/0212397 A1 | 11/2003 | Avrahami et al. | |
| 2004/0181203 A1 | 9/2004 | Cormier et al. | |
| 2004/0204669 A1 | 10/2004 | Hofmann | |
| 2004/0236271 A1 | 11/2004 | Theeuwes et al. | |

FOREIGN PATENT DOCUMENTS

| | | |
|---|---|---|
| DE | 196 24 578 A1 | 1/1998 |
| EP | 0 312 662 A1 | 4/1989 |
| EP | 0 407 063 A1 | 1/1991 |
| EP | 0 796 128 B1 | 11/1995 |
| EP | 1 086 719 A1 | 3/2001 |
| EP | 1 174 078 A2 | 1/2002 |
| FR | 2535602 A1 | 11/1984 |
| GB | 783479 | 9/1957 |
| GB | 2221394 A | 2/1990 |
| JP | 09-051878 | 2/1997 |
| SU | 1 667 864 | 7/1991 |
| WO | WO 93/17754 A1 | 9/1993 |
| WO | WO 94/23777 A1 | 10/1994 |
| WO | WO 95/33612 A1 | 12/1995 |
| WO | WO 96/00109 A1 | 1/1996 |
| WO | WO 96/37155 A1 | 11/1996 |
| WO | WO 96/37256 A1 | 11/1996 |
| WO | WO 97/03718 A1 | 2/1997 |
| WO | WO 97/48440 A1 | 12/1997 |
| WO | WO 97/48441 A1 | 12/1997 |
| WO | WO 97/48442 A1 | 12/1997 |
| WO | WO 98/00193 A1 | 1/1998 |
| WO | WO 99/00155 A1 | 1/1999 |
| WO | WO 99/29298 A2 | 6/1999 |
| WO | WO 99/29364 A1 | 6/1999 |
| WO | WO 99/29365 A1 | 6/1999 |

| WO | WO 99/64580 A1 | 12/1999 |
| WO | WO 00/05166 A1 | 2/2000 |
| WO | WO 00/35530 A1 | 6/2000 |
| WO | WO 00/74763 A2 | 12/2000 |
| WO | WO 00/74765 A1 | 12/2000 |
| WO | WO 00/74766 A1 | 12/2000 |
| WO | WO 02/07813 A1 | 1/2002 |
| WO | WO 02/32331 A2 | 4/2002 |
| WO | WO 02/72189 A2 | 9/2002 |
| WO | WO 03/24290 A1 | 3/2003 |
| WO | WO 03/24518 A2 | 3/2003 |

OTHER PUBLICATIONS

Sebastian, H. et al., "Microfabricated Microneedles: A Novel Approach to Transdermal Drug Delivery", Journal of Pharmaceutical Sciences, Aug. 1998, pp. 922-925, vol. 87, No. 8, Atlanta, GA.

Chun, K. et al., An Array of Hollow Microcapillaries for the Controlled Injection of Genetic Materials into Animal/Plat Cells, The University of Tokyo.

Wouters, S. et al., "Microelectrochemical Systems for Drug Delivery", Electrochimica Acta., 1997, pp. 3385-3390, vol. 42. Nos. 20-22.

Prausnitz, M. R., et al., "Transdermal Delivery of Macromolecules: Recent Advances by Modification of Skin's Barrier Properties", Therapeutic Protein and Peptide Formulation and Delivery, pp. 124-153, Chapter 8, ACS Symposium Series 675, Georgia Institute of Technology.

Prausnitz, M. R., et al., Transdermal Transport Efficiency During Skin Electroporation and Iontophoresis, Journal of Controlled Release 38, 1996, pp. 205-217, Massachusetts Institute of Technology, Cambridge, MA.

Papautsky, I. E., et al., "Micromachined Pipette Arrays (MPA)", pp. 2281-2284, Proceedings 49 International Conference—IEEE/EMBS Oct. 30-Nov. 2, 1997, Chicago, IL.

* cited by examiner

MICROSTRUCTURES FOR DELIVERING A COMPOSITION CUTANEOUSLY TO SKIN

CROSS REFERENCE

This application claims the benefit of U.S. Provisional Application Ser. Nos. 60/240,730 and 60/240,787 both filed on Oct. 16, 2000.

TECHNICAL FIELD

The present invention relates generally to systems that deliver a composition into skin and is particularly directed to an article of manufacture of the type which is used to deliver a composition cutaneously (or subcutaneously) into skin. The invention is specifically disclosed as a planar array of microelements that are capable of lancing the surface of skin and penetrating the surface of skin to a depth where a composition can be efficaciously applied. The article of manufacture is capable of delivering a composition from a reservoir attached thereto, or the composition can be applied directly to skin and utilized therein in combination with the article of manufacture.

BACKGROUND OF THE INVENTION

Human skin is the largest organ. Aside from the function of regulating skin temperature, the skin's most important function is to serve as an effective barrier against insult of the body by foreign agents, such as toxic substances, microorganisms, and due to mechanical injury. Human skin comprises several layers: the outermost is the stratum corneum, which comprises dead skin cells and makes up a substantial portion of the first protective barrier of the body. Most skin comprises a stratum corneum which is 15–20 layers of dead cells thick (about 10–20 microns in thickness). However, some "durable" skin layers, such as heels or calluses, can comprise a stratum corneum which is from 100–150 microns thick. On average, the skin naturally sheds at least one skin layer each day, and the first one to four layers of skin may be removed without affecting the protective nature of skin or the health thereof In fact, removing up to four (4) layers of the stratum corneum may provide a skin surface area onto which make-up may be more uniformly applied and once applied has a more aesthetically pleasing appearance.

Penetration of the outer layers of skin to deliver a pharmaceutical composition is a widely held practice. Typically injections of pharmaceuticals are affected by subcutaneous delivery, intramuscular delivery, as well as intravenous delivery. Less invasive procedures have now been developed and are widely utilized. Among these "topical" applications are patches, which are used to provide slow release of a composition, such as air and motion sickness compositions, or cigarette smoking abatement compositions. However, these patch delivery systems rely on formulations that can carry the active ingredients across the skin barrier into the blood stream. Therefore, formulation and dosing limitations may provide an encumbrance to delivery of a medication or skin benefit composition via patch.

There is, therefore, a long felt need for an article of manufacture that can be used to deliver a composition cutaneously (or subcutaneously) to skin. Specifically, there is also a need for article that is capable of lancing the surface of skin or is capable of penetrating the surface of skin to a depth where a composition can be efficaciously applied.

One solution to the above-noted long felt need is a "patch" that contains a plurality of microneedles, in which each individual microneedle is designed to puncture the skin up to a predetermined distance, which typically is greater than the nominal thickness of the stratum corneum layer of skin. Using such microneedle patches provides a great benefit in that the barrier properties of the skin can be largely overcome, while at the same time the microneedles can be painless and bloodless if they are made to not penetrate through the epidermis.

One problem with microneedles is that, first they require a direct pushing motion against the skin, which may or may not be of sufficient force to penetrate completely through the stratum corneum and, second even when they do penetrate the stratum corneum, their efficiency of compelling a fluid (such as a liquid drug or other active) though their relatively tiny openings is not great (these microneedles are usually quite small in diameter). It would be an improvement to provide a microstructure (e.g., in the form of a hand-held patch) that can provide a greater efficiency of flow for some type of fluidic compound through the stratum corneum, and to make it possible for the microstructure to penetrate the outer skin layers (e.g., the stratum corneum) by a sliding or rubbing motion that is essentially parallel to the skin surface, rather than perpendicular to the skin surface. The sliding/rubbing motion allows each microelement protruding from the substrate (or base) of the microstructure to make multiple slits or cuts in the outer layers of the skin, which increases the permeability of the skin (i.e., it reduces the skin's barrier properties) at that local area.

SUMMARY OF THE INVENTION

Accordingly, it is an advantage of the present invention to provide a method and apparatus that can deliver either a benefit to human skin or deliver a composition cutaneously into skin.

It is another advantage of the present invention to provide an article of manufacture that is capable of lancing the surface of skin, or of penetrating the surface of skin to a depth where a composition can be efficaciously applied.

It is a further advantage of the present invention to provide an article of manufacture that is capable of repeatedly penetrating the skin to a predetermined depth, thereby providing a means for delivering a composition to the sub stratum corneum layer.

It is still a further advantage of the present invention to provide an article of manufacture that can be applied to the surface of skin and used to controllably release a composition over a protracted period of time.

It is yet another advantage of the present invention to provide a microstructure as an article of manufacture that penetrates the outer skin layers by a sliding or rubbing motion that is essentially parallel to the skin surface, rather than perpendicular to the skin surface.

It is yet a further advantage of the present invention to provide a microstructure that penetrates the outer skin layers by a sliding or rubbing motion so that each microelement protruding from the substrate of the microstructure can make multiple slits or cuts in the outer layers of the skin, and thereby increase the permeability of the skin.

Additional advantages and other novel features of the invention will be set forth in part in the description that follows and in part will become apparent to those skilled in the art upon examination of the following or may be learned with the practice of the invention.

To achieve the foregoing and other advantages, and in accordance with one aspect of the present invention, a method for reducing the barrier properties of skin is provided, in which the method comprises the steps of: (1) providing a microstructure having a substrate and a plurality of microelements that protrude from the substrate by at least one predetermined protrusion distance; and (2) placing and rubbing the microstructure on skin, in which the rubbing motion occurs in a direction that is substantially parallel to a surface of the skin, and wherein the at least one predetermined protrusion distance is sufficient so that many of the plurality of microelements penetrate a stratum corneum layer of the skin.

In accordance with another aspect of the present invention, an improved microstructure apparatus is provided, which comprises: a substrate and a plurality of microelements affixed upon a first surface of the substrate; in which the plurality of microelements are of predetermined sizes and shapes so as to penetrate a stratum corneum layer of skin when the microstructure apparatus is placed upon the skin and moved in at least one predetermined direction, wherein the at least one predetermined direction is in a direction that is substantially parallel to a surface of the skin.

The present invention relates further relates to embodiments of the article of manufacture which allows sustained cutaneous delivery of a enhancing composition, pharmaceutical composition, or the like.

Still other advantages of the present invention will become apparent to those skilled in this art from the following description and drawings wherein there is described and shown a preferred embodiment of this invention in one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

All percentages, ratios and proportions herein are by weight, unless otherwise specified. All temperatures are in degrees Celsius (° C.) unless otherwise specified. All documents cited are in relevant part, incorporated herein by reference.

BRIEF DESCRIPTION OF THE DRAWINGS

The accompanying drawings incorporated in and forming a part of the specification illustrate several aspects of the present invention, and together with the description and claims serve to explain the principles of the invention. In the drawings:

DETAILED DESCRIPTION OF THE INVENTION

Figure 1:
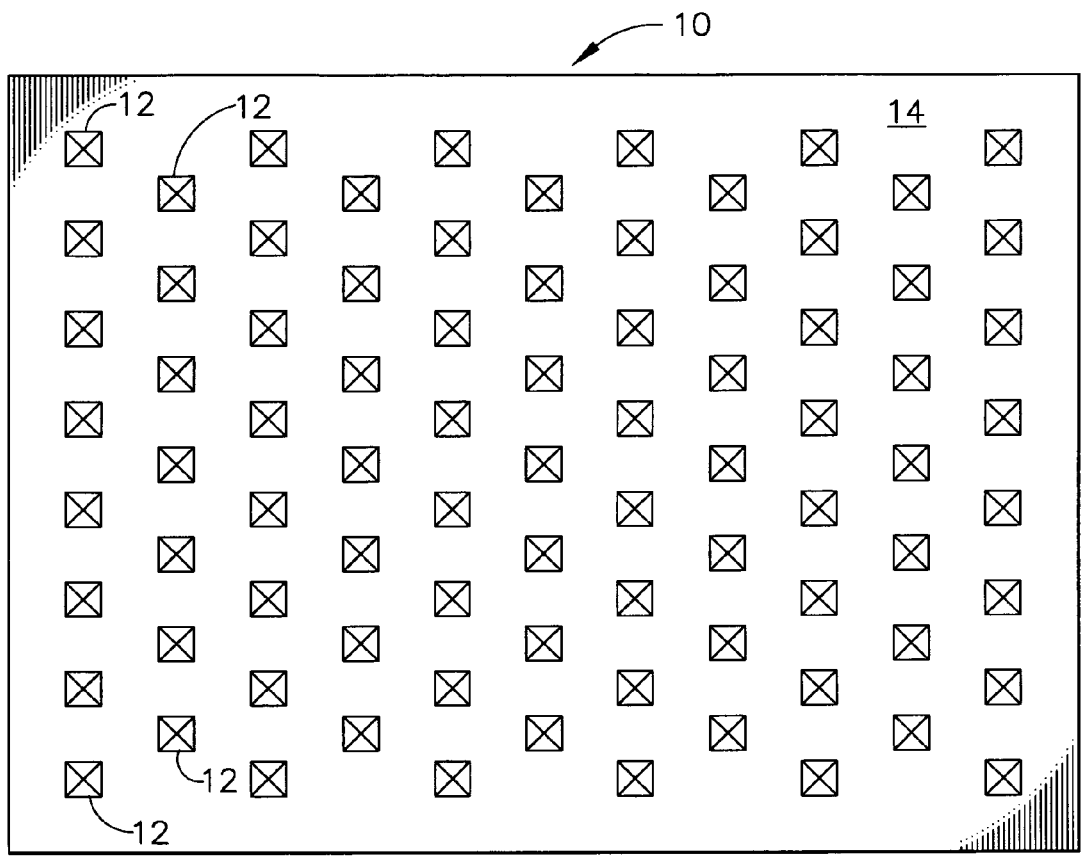
FIG. 1 is a plan view of an array of microelements that are pyramidal in shape, as constructed according to the principles of the present invention.

Reference will now be made in detail to the present preferred embodiment of the invention, an example of which is illustrated in the accompanying drawings, wherein like numerals indicate the same elements throughout the views.

The present invention relates to cutaneous delivery of a composition to the body by way of an article of manufacture, which controllably penetrates the outside layers of human skin. The present invention further relates to an embodiment wherein the article of manufacture remains attached to the skin surface and is capable of protracted delivery of a composition, or protracted sampling of a biological fluid, such as interstitial fluid.

For the purposes of the present invention the term "cutaneous delivery" is defined as "a composition which is controllably delivered to human skin by an article of manufacture wherein the article of manufacture is capable of penetration of the skin layer to a finite depth without producing concomitant trauma." The words cutaneous and, subcutaneous are essentially interchangeable terms as used herein. The term "trauma" is defined herein as "pain associated with the application of the article of manufacture to the surface of skin, bleeding, bruising, swelling, damage to skin areas, and the like."

Self-administration of drugs is a necessity for many individuals. Aside from topically applied medication treating skin itself, most medications are self-administered orally. However, there is wide recognition that some categories of formulations, such as pharmaceutical formulations, are best administered directly into body tissue, for example, intravenous (IV), intramuscular (IM) injections. When applying both IV and IM injection techniques, there are a number of considerations. For example, the skill of administering person, the will of a patient to self-administer an injection, or the effectiveness of the patient's self-delivery must be considered when prescribing a treatment plan.

These issues can be held in abeyance and compositions, pharmaceutical or otherwise, can be delivered routinely to humans without the concerns of pain, swelling, trauma, or lack of compliance by the patient. In addition, the inconvenience of storing and re-supplying of syringes, swabs, and the like are made unnecessary by the systems and principles of the present invention.

The stratum corneum of skin comprises layers of dead skin cells, which are part of the body's protective outer layer. This outermost layer of skin cells can have a nominal thickness of from about one hundred (100) microns to about 250 microns for thick, durable skin areas, such as calluses, whereas normal, "thin" skin may comprise from about ten to about fifteen microns (10–15) thickness for its stratum corneum. One aspect of the present invention relates to the penetrating or piercing the stratum corneum. The articles of manufacture described herein can be configured to provide various sizes and shapes of penetrating microelements. One way this is achieved is by adjusting the configuration of the microelements and/or the distance from which the distal end of the microelements protrude from a particular base element.

By adjusting the configuration of the penetrating microelements, not only is the depth of skin penetration modulated, but also the type of penetration can be adjusted. For example, the articles of manufacture of the present invention may have hollow or grooved penetrating microelements, which can serve as passages through which a substance may flow. These passages allow for transport of a composition to the skin, for example, a pharmaceutical, preferably without bleeding, pain, or other associated trauma. The terms "microelement" and "penetrating microelement" are interchangeable as used herein.

Articles of Manufacture

The articles of manufacture of the present invention comprise a base element (or "substrate") onto which is affixed or deposed a plurality of microelements. The following is a description of the base element and corresponding microelements.

Base Element

The articles of manufacture of the present invention comprise at least one base element having a first side and a second side. Onto the first side are affixed the penetrating microelements as described hereinbelow. Aside from providing a template or base structure onto which the microelements are affixed, the second side, or reverse side, may in turn comprise a handle or other means by which the article of manufacture can be held. In another embodiment, a substance can be deposed upon the second side, which allows the user to grasp, hold, or otherwise control the motion of the article using only the fingertips. The use of a material to provide a tactile surface is especially compatible for embodiments wherein the base element comprises a thin, flexible material, such as paper or polymeric sheets. One embodiment of the present invention includes base elements which comprise flexible sheets, and the thickness of the sheets is determined by the desired degree of flexibility. The flexible sheets are typically rigid enough to provide a template upon which the microelements can be affixed, but which are easily deformed to fit the contours of the skin surface.

The base elements of the present invention may have any shape or configuration. For example, one embodiment relates to circular base elements, while another embodiment relates to rectangular base elements having a width and a length. For such articles of manufacture that comprise microelements having a "microelement angle" less than 90° as defined hereinbelow, rectangular base elements will have a left edge and a right edge. The right edge of the base element is defined herein as the edge along the right side of the base element when the second side of the base element is facing down (away from the observer) and the first side is facing the observer. The left edge is oppositely defined herein.

In another embodiment of the present invention, the second side may have a reservoir (or chamber) attached thereto (or constructed therewith) which contains a flowable (or "fluidic") composition, or at least one reservoir or chamber for receiving material (e.g., interstitial fluids) removed from skin. For embodiments of this type, it is an option to modify the base element to comprise a plurality of hollow elements, or to provide channels or pore openings along with solid microelements. Such hollow elements or channels would ostensibly provide a means for a deliverable material or removable material to flow from the first side of the base element to the second side, or vice versa. The hollow elements can also be in register with a hollow element, channel, hole, or other passageway which modifies the microelements as described hereinbelow in a manner that allows a flowable composition to be delivered from the reservoir through a hollow element in the base element, through a tube or channel of the microelement, and into skin.

For purposes of the present invention, the terms "fluid" or "fluidic" have a meaning that includes flowable liquids, flowable gases, relatively low-viscosity creams, flowable solutions that may contain solid particles, and the like. A "fluidic compound" or "fluidic material" specifically includes such liquids, gases, and solutions; these compounds or materials may comprise an active, a drug, or a skin conditioner, or other useful composition of matter; alternatively, the term "fluidic compound" can represent at least two actives, drugs, or the like, including both a biological active and a chemical active (in a single fluidic compound).

Penetrating Microelements

The articles of manufacture of the present invention further comprise a plurality of penetrating microelements, which are affixed to the first side or first surface of the base element. The "proximal end" of the microelement is defined herein as "the penetrating microelement end, which is affixed to or in register with the base element." The "distal end" of the penetrating microelement is defined herein as "the penetrating microelement end which comes into contact with skin, and which is the opposite end of the microelement from the proximal end." The term "penetrating microelement" is defined herein as "an appendage for contacting skin which extends from the first side of the base element and is affixed thereto (or protrudes therefrom) at an attachment angle." The term "penetrating microelement" refers to the entire element which contacts the skin and includes not only the appendage itself, but the attachment angle, any hollow elements or grooves, the density of the microelements as measured in the number of appendages per square centimeter, and any pre-disposed composition of matter on the microelement surface.

The general purpose of the penetrating microelement is to lance, cut, or otherwise open the outer layers of skin to a predetermined depth or configuration in order to deliver a composition. In one embodiment of the present invention, the penetrating element is durable and can, therefore, be reused; however, embodiments which are disposable are also encompassed by the present invention, and do not reqqire cleaning or sterilization after use.

For the purpose of the present invention the term "lancing" (or "cutting") is used herein to define the use of a "penetrating element that has a predetermined height and width, wherein the skin is cut to a predetermined limited depth and a predetermined slit opening width as even pressure and sliding force is applied by the microstructure patch to the skin surface by the user, in which the depth and slit opening width of the cut made by the microelement directly corresponds to the skin healing time (i.e., the time required for the skin to recover its barrier properties)." Lancing elements are typically use to penetrate the easily cut tissue or tissue which is mechanically damaged, for example, an infected area of the skin which is tender to the touch or which has scab formation proximal to the area to be treated. In addition, penetrating elements which "lance" may be more suitable for articles of manufacture that are used to treat skin grafts or tissue damaged by heat, such as in first degree or second degree burns.

The term "lancing" typically connotes a single effective stroke, whereas a "sawtooth" penetrating element is used to penetrate skin that is more durable and resistant to mechanical pressure, although such sawtooth motion can also be used on normal "thin" skin. Embodiments of the present invention that employ sawtooth motions can be used in "durable areas" of the skin, and include the heel and toe areas, as well as, calluses, corns, and the like. Virtually all embodiments of the present invention can be used with either a single penetrating stroke, or with a back and forth (or "sawtooth") motion against the surface of skin.

As used herein, the term "rubbing" represents an action by which one of the microstructures of the present invention is placed upon skin and moved along the surface of the skin. The rubbing action can be achieved manually, or by using a device. In other words, the microstructure can be held by hand and manually rubbed against the skin, or the microstructure can be placed on a mechanical device that will, in turn, be used to move (or rub) the microstructure upon the surface of the skin.

The term "skin" is defined herein as "animal skin, including human skin, plant skin or surfaces, and even other biological structures that may not have a true "skin" organ, such as tissue samples of either plant or animal origin."

For the purposes of the present invention, the term "affixed" as it relates to attachment of the microelements to the base element is defined as "held permanently to the first side of the base element." Affixed microelements are neither removable nor detachable. The microelements of the present invention, as it relates to the term "affixed," can comprise any suitable embodiment. For example, the microelements and base element may comprise a single uniform composition or the microelements may be extruded from the material comprising the first side.

Alternatively, and in a separate embodiment, the microelements may be applied to the base element in a separate operation or manufacturing step, such as lamination to a non-woven substrate. Therefore, the microelements can be fashioned and applied in any manner the formulator desires which achieves the desired microelement density or configuration, or which achieves the desired penetrating properties. Other suitable microelement configurations include those described in United States patent applications: U.S. Ser. Nos. 09/580,780, 09/580,819, and 09/579,798 all filed May 26, 2000; U.S. Ser. No. 09/614,321 filed Jul. 12, 2000 all of which are commonly-assigned to The Procter & Gamble Company, and which are incorporated herein by reference.

For the purposes of the present invention the term "microelement density" is defined herein as "the number of microelements per square centimeter of base element surface."

The appendages that comprise the microelements may be of any configuration that is capable of providing the desired skin penetration necessary to deliver a composition or treatment. One embodiment of the present invention relates to a plurality of appendages in the form rod-shaped appendages that are either circular or elliptical, perhaps having a uniform circumference along the entire length. Planar appendages include cubes or cubic rectangles (or open boxes) wherein the length and width are uniform (but not necessarily equal to one another) throughout the height of the appendage and the distal end comprises a plane, such as a square, rectangle, or trapezoid, in which the plane is parallel to the base element or at an angle thereto. Wedge-shaped appendages have a rectangular proximal base that tapers to a line segment, which preferably has the same length as the length of the rectangular base. Some wedge-shaped appendages may have an inverted appearance. Pyramidal appendages may comprise bases which have three or four sides at the proximal end base, and which taper to a point or rounded top at the distal end. Alternatively, the wedge-shaped appendages may have a triangular section removed therefrom that acts to facilitate the removal of skin hair follicles. The appendages of the present invention may also be coiled or otherwise arcuate, having any number of turns from the proximal end to the distal end.

One embodiment of the present invention relates to a plurality of lancing elements arranged laterally across the front edge of the base element. Sawtooth-like embodiments may have the "teeth" varied in a variety of ways, for example, the size (height) of the teeth, the spacing between teeth, and whether the ends of the teeth are tapered to a more narrow width. Other penetrating elements include square or rectangular posts, blades (circular and straight), straight or curved wedges, or pyramidal-, cylindrical-, cube-, and star-shaped elements.

For the purposes of the present invention the term "penetrating element angle" is defined as the "angle at which the appendage of the penetrating microelement protrudes from the base element." For example, a microelement, which is affixed perpendicular to the base element, has a penetrating element angle of 90°. The microelements of the present invention can be affixed to the base element at any angle from about 30° to about 90° (perpendicular). However, if the direction of use of the article of manufacture is not symmetrical, the microelements can be affixed to the base element at any angle from about 30° to about 150°. In addition, microelements which are not perpendicular to the base element may be angled toward any edge of a rectangular or square base element, or be perpendicular to the tangent of any point along the circumference of a circular base element.

The penetrating microelements of the present invention may also comprise hollow elements or contain grooves. Hollow elements are typically disposed along the longitudinal axis of the appendage portion of the microelement and are in register with a corresponding hollow element or passageway at the base element. Grooves or indented elements occur along the surface of an appendage and serve, like hollow elements, to provide a means for a solution to be delivered into the fissures created by the penetrating elements. Embodiments having at least one reservoir or chamber can deliver a fluidic compound into the skin.

The microelements of the present invention may range from absolute rigid (inflexible) to flexible. For the purposes of the present invention, the term "flexible" is defined herein as "during use against skin, the distal end of an appendage is bent or deformed up to 90° from the microelement angle as defined herein above." A perpendicular appendage which is bent 90° is therefore parallel with the base element. An appendage having a microelement angle of 45° can be deformed or bent to an angle of 135°. It will be understood, however, that the penetrating microelements that cut into skin, as discussed below, are typically non-rigid in nature.

The penetrating elements of the present invention may have a protrusion distance of up to 1000 microns from the surface of the base element. The term "protrusion distance" is defined herein as "the distance from distal end of the penetrating microelement along a line parallel to the base element." For perpendicular microelements the length of the appendage and the protrusion distance are equivalent. A microelement having a microelement angle, for example, of 30° will have a protrusion distance equal to one half the length of the appendage.

One embodiment of the present invention relates to microelements having a protrusion distance of about 1–1000 microns. Another embodiment relates to protrusion distances of about 1–200 microns. Further embodiments encompass penetrating microelements wherein the appendages have protrusion distances from about one to about twenty (1–20) microns, whereas other embodiments include protrusion distances of from about five to about twenty (5–20) microns and from about four to about twenty (4–20) microns, as well as embodiments from about four to about ten microns (4–10). Other embodiments comprise no range of protrusion distances but have discreet distances, for example, a 4-micron embodiment, a 5-micron embodiment, a 10-micron embodiment.

The penetrating microelements of the present invention may comprise an appendage which has flexible elements and rigid elements such as, for example, an appendage which has a rigid portion extending from about the middle of the element to the proximal end and a flexible portion extending from about the middle of the element to the distal end. Articles of manufacture which are composites of several materials may comprise a thin flexible base element onto which are deposed rigid, inflexible penetrating elements. As noted above, most of the penetrating microelements described herein will be rigid in nature.

The articles of manufacture of the present invention may comprise a multitude of arrays, each array comprising the same or different types or sizes of microelements, in which the various attributes of the microelements, including microelement density, appendage type, microelement angle, hollow elements vs. solid elements with or without grooves, degree of flexibility, protrusion distance, etc. may vary from array to array or within a single particular array. For the purposes of the present invention the term "array" is defined as "multiple microelements in a pattern."

In some cases, certain array elements collectively may be separated from another array by a distance which is greater than the distance between the microelements which comprise the first array. In other cases, arrays may contain different types of microelements which all have the same spacings. The distance between microelements along the edge of two separate and distinct arrays may be greater than the distance between two microelements, which are members of the same array. Alternatively, several different microelement shapes or protrusion sizes may exist in a single array in which all individual elements are spaced-apart from one another in a consistent manner throughout the entire structure.

The microelements preferably have a length and shape that will tend to penetrate entirely through the stratum corneum layer by a cutting ("lancing"), slitting, or plowing motion. The characteristic of the microelements to cut and penetrate entirely through the stratum corneum is further enhanced by directing the user to move the "patch" or microstructure substantially in only one direction (or substantially along a single line that represents a back and forth direction), so that the "sharper" edges of the microelements tend to cut or plow into the skin upper layers. This allows a liquid or cream-like substance (i.e., a fluidic compound) to be placed into the slits or cuts made in the stratum corneum, and greatly enhances the amount of such fluid or cream (e.g., an active, drug, or other compound) to enter through the stratum corneum. Furthermore, so long as the penetration depth is properly controlled (which is accomplished by providing microelements having proper shapes and lengths), the skin heals very quickly; in some circumstances, the skin's barrier properties recover in less than two hours!

The methodologies for using "solid" microelements are expected by the inventors in two main embodiments: (1) first to cut (or "lance") the skin using the microstructure (or patch), then apply a fluidic material (such as an active) onto the same skin area after withdrawing the microstructure patch, and the fluidic material will tend to penetrate into the stratum corneum through the slits just previously made; or (2) first to apply the fluidic material onto the skin and then place the microstructure patch upon the same skin area and cut (or lance) the skin, thereby assisting (or forcing) the fluidic material to penetrate through the stratum corneum.

A further methodology for use involves microelements having holes or slots therethrough, or through-holes in the substrate adjacent to the microelements. In this embodiment of use, the skin is cut ("lanced") and a fluidic material is applied through the holes/slots in a single procedural step. Of course, the skin must first literally be slit or cut through its stratum corneum layer before the fluidic material can flow through the slits formed therein, but this essentially can occur virtually simultaneously while the user makes a single back and forth set of movements (or perhaps even a single stroke in only one direction would suffice in certain physical configurations of microstructures). A reservoir of some type to hold the fluidic material would be required as part of the microstructure patch in this methodology, although there are variations available as to the exact construction of such a reservoir, as described below.

Referring now to the drawings, FIG. 1 illustrates a microstructure array generally designated by the reference numeral 10 containing multiple microelements 12 that are situated on a base or substrate 14. In FIG. 1, each "column" of microelements 10 is offset from the next, adjacent column of similar microelements. However, each of the columns could be made to be identical to one another, if desired, and the offset could be removed. Alternatively, there could be several columns with various offsets before the microelement pattern repeats, or the offsets could be substantially random so that there is no repetitive pattern.

Figure 2:
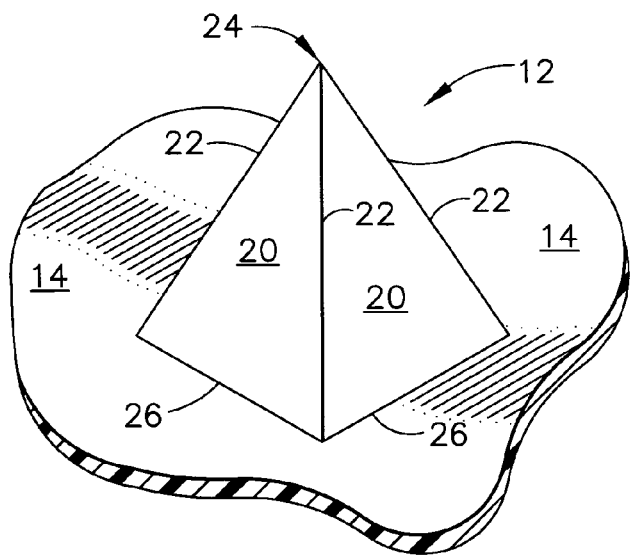
FIG. 2 is a perspective view of one of the pyramidal microelements of FIG. 1.

FIG. 2 illustrates in a magnified view one of the microelements 12, which has the appearance of a four-sided pyramid. Each side wall of the pyramid is designated at the reference numeral 20, and the seam or "corner" between sides is located at the reference numeral 22. The pyramid's peak is illustrated at 24, and the base line of each of the sides is located at 26, where it meets the substrate 14.

This array 10 of microelements is very useful in penetrating the stratum corneum layer of skin by forming it into a patch that can be held by a human hand, and placed against a particular area of skin and then rubbed in a straight back and forth motion (or perhaps in a circular motion, if desired). When the patch or array 10 is rubbed against the skin, the microelements 12 will tend to penetrate into the dead skin cells, and will do so with a lateral, sliding motion (that is substantially parallel to the skin surface) instead of using a pushing or thrusting motion (that is basically perpendicular to the skin surface).

The array or patch 10 will correctly perform its functions of penetrating through the stratum corneum without regard to the direction of movement of the patch 10 with respect to the orientation of the individual microelements 12. In other words, these microelements 12 are omnidirectional in operation, and all directions are preferred, or even "predetermined." Other embodiments of the invention described below are not omnidirectional, and instead are unidirectional or bi-directional in nature with respect to the orientation of their individual microelements.

The microelements will cut into the skin to a predetermined "penetration depth," which will be controlled by (and probably substantially equivalent to) the "protrusion distance" of the microelements 12. Other embodiments of the present invention, as described below, will function in a like manner.

Another feature of the microstructure 10 is its capability for use in applying a conditioner or other type of compound that is in the form of a liquid or a cream. Just after the microstructure patch 10 has penetrated an area of skin, the stratum corneum will have numerous slits or cuts therewithin, which significantly reduces (at least temporarily) the skin's barrier properties. A fluidic compound can now be applied to the skin, which will much more readily make the journey into the epidermal layer. The fluidic compound could be some type of drug or other active, if desired. The other microstructures described below will also lend themselves well for this type of topical application of a fluidic compound to penetrate into skin.

A further feature of the microstructure 10 is its capability for a compound to be applied onto the substrate 14 and/or microelements 12 in advance of its placement against an area of skin. When the microstructure patch 10 is placed onto the skin, it will impart some of this compound onto the same area of the skin that is being penetrated-this will essentially occur simultaneously. The other microstructures described below will also lend themselves well for this type of simultaneous delivery of a fluidic compound to the same area of skin that is being penetrated. Of course, the embodiments described below which include through-holes in the substrate (e.g., see FIGS. 3 and 4) may not be the first choice for this methodology of composition delivery, but such devices certainly could be used in this manner, if desired. The compound that is pre-applied to the surface of the microstructure 10 could be placed either by the user, or at the time of manufacture of the microstructure 10.

Figure 3:
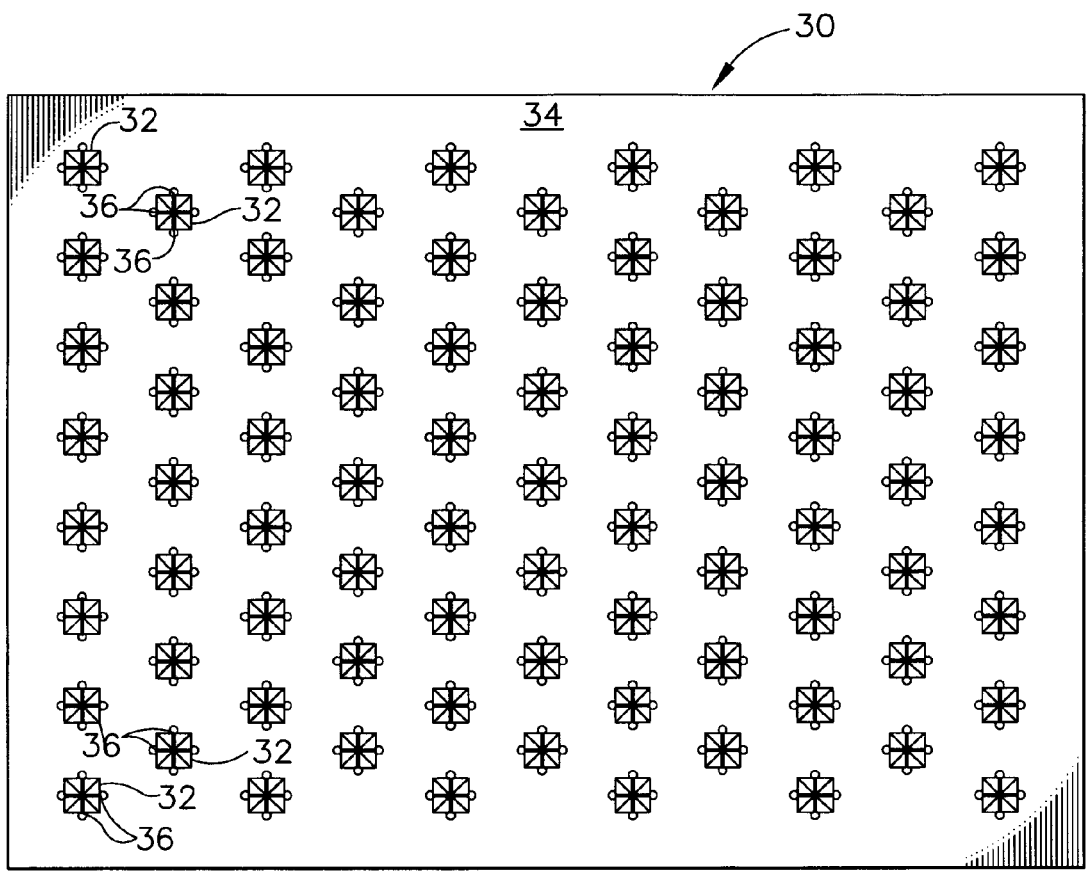
FIG. 3 is an array of pyramidal microelements as according to FIG. 1, with the addition of through-holes in the substrate, and channels along the sides of the microelements.

FIG. 3 illustrates a similar microelement array, generally designated by the reference numeral 30, in which through-holes and channels are added. The base or substrate 34 includes a plurality of through-holes 36 that are positioned proximal to the base of the individual pyramidal microelements 32. These through-holes 36 can either penetrate through the entire substrate 34, or can penetrate partially into the substrate and connect to passageways that may run in a direction perpendicular to the through-holes, and make common connections between many of the through-holes.

Figure 4:
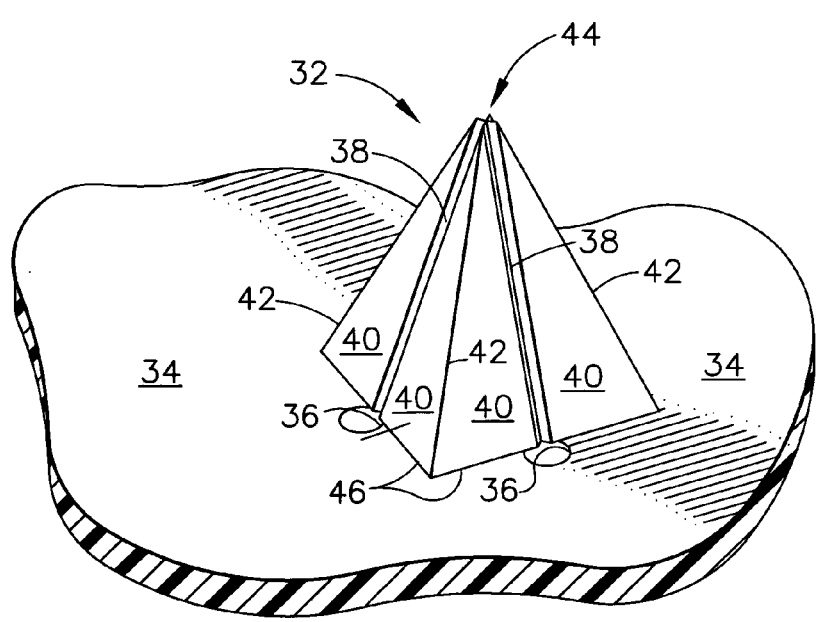
FIG. 4 is a perspective view of the pyramidal microelements of FIG. 3.

On FIG. 4, further details are visible, in which the side walls 40 of the pyramidal microelement 32 are seen to have grooved channels 38 which connect to the through-holes 36. The edges of the side walls 40 are at reference numeral 42, the individual base lines of the pyramid are at 46, and the peak of the pyramid is at 44.

On FIGS. 3 and 4, the array 30 of multiple pyramidal structures at 32 all have a through-hole adjacent to each side of the pyramid. Of course, there could be fewer through-holes 36 per pyramidal microelement 32, if desired. Alternatively, some of the pyramidal microelements 32 in the array could have no adjacent through-holes, if desired. Such microelements (or others in the array) could also forego the channels 38.

The structure of FIGS. 3 and 4 is useful to perform a simultaneous penetration and drug delivery step. While the array or "patch" 30 is rubbed along the skin, the skin cells of the stratum corneum will be cut, lanced, or slit (or otherwise penetrated) by the individual pyramidal microelements 32, which will prepare the skin for any type of fluidic compound that will then be "injected" through that area of skin surface. A capillary force will work to the advantage of delivering a drug or other active. Of course, mechanical pressure or iontophoresis could be used to assist in the delivery, for example.

It will be understood that instead of delivery of a fluidic compound such as a drug into the skin, the microstructures disclosed in FIGS. 3 and 4 could be used to sample an interstitial fluid, for example. In that event, the fluid flow would of course be in the opposite direction through the through-holes 36, and would subsequently be directed to a collecting reservoir or chamber, as for example, is described below.

Similar to the patch 10, the array or patch 30 will correctly perform its functions of penetrating the skin cells of the stratum corneum without regard to the direction of movement of the patch 30 with respect to the orientation of the individual microelements 32. In other words, these microelements 32 are omnidirectional in operation, and all directions are preferred, or even "predetermined."

Another potential use of the array or patch 30 is to attach the entire microstructure patch to skin for an relatively lengthy time interval, and thereby provide a capability for protracted delivery of the fluidic compound into the epidermis, using the cuts or slits that were formed during the previous rubbing procedure. It also would be possible to sample biological fluids for a prolonged time interval by attaching the microstructure patch to the skin. Moreover, it would be possible to have simultaneous interstitial fluid sampling and drug delivery (of insulin, for example) by this arrangement, particularly if more than one set of holes in a microelement were provided (see other such structures, below), or if at least two groups of microelements were provided on a single substrate. A first group (or array) could sample the interstitial fluid, while a second group (or array) could delivery the drug.

Figure 5:
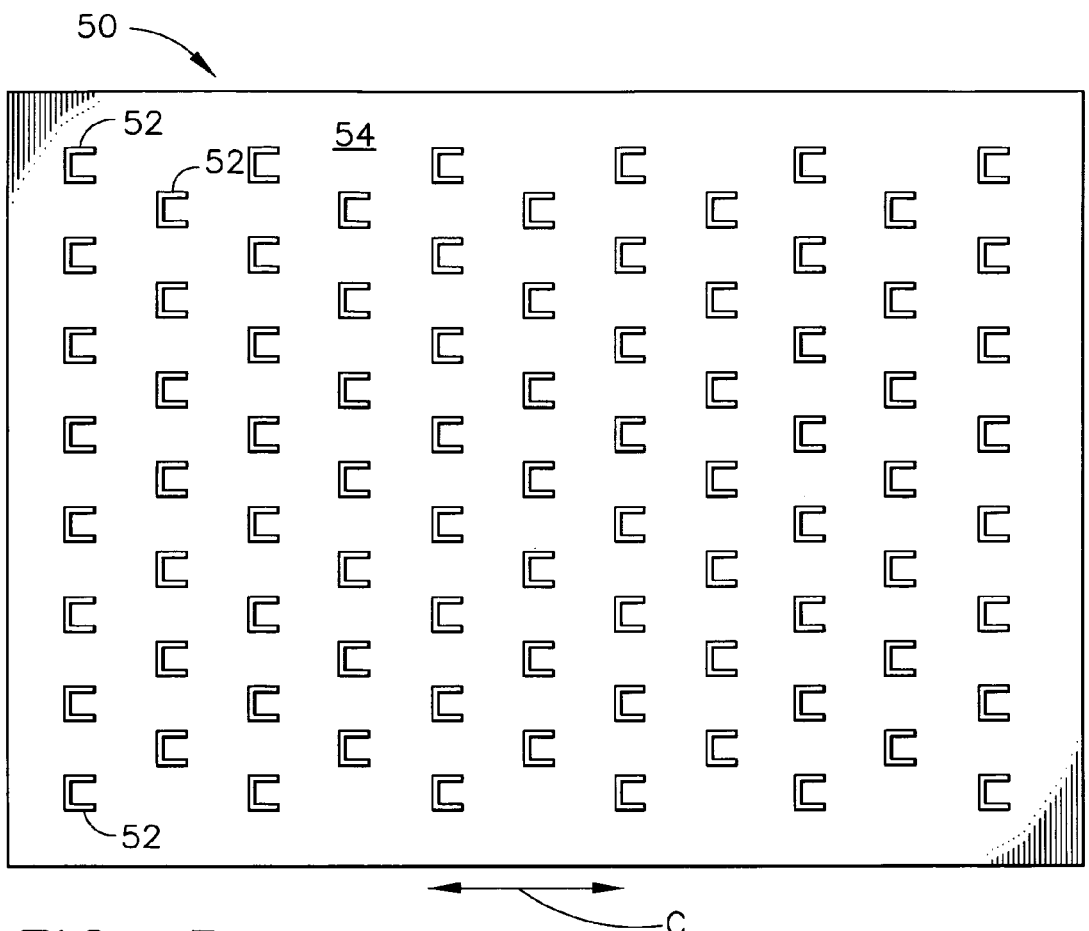
FIG. 5 is a plan view of an array of microelements that have an overall cubic rectangular shape, as constructed according to the principles of the present invention.

Another microelement shape is illustrated in FIG. 5, comprising an array 50 of "cubic rectangular" microelements at 52. These microelements 52 have a cup-like shape which has the appearance of a topless, hollow or open cube-like or box-like structure after one of the cube's (box's) side walls have been removed. This can be clearly seen in the perspective view of FIG. 6. (It will be understood that the "cube-like structure" 52 does not have identical length, width, and height outer dimensions, and thus is not really a geometric cube. In that respect, the term "box-like" or "box" is more descriptive.)

The individual columns of microelements 52 can be offset on the substrate 54, as seen in FIG. 5. As an alternative construction, each of the individual columns of these microelements 52 could be identical, thereby eliminating any offset, if desired. As a further alternative, there could be several columns with various offsets before the microelement pattern repeats, or the offsets could be substantially random so that there is no repetitive pattern.

Figure 6:
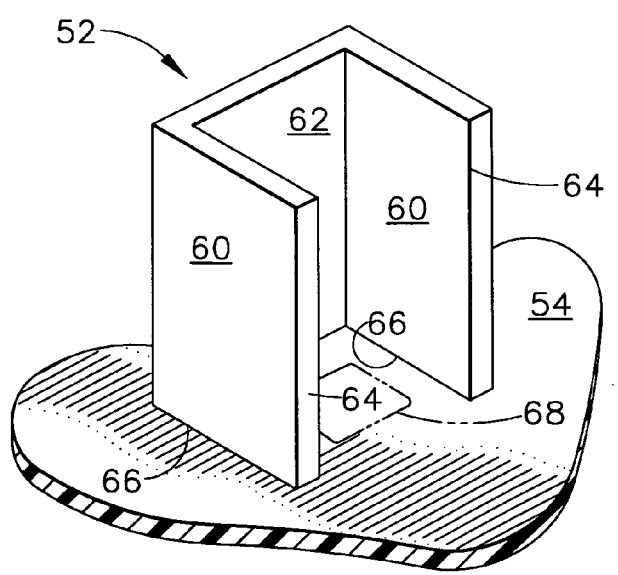
FIG. 6 is a perspective view of one of the cubic rectangular microelements of FIG. 5.

FIG. 6 shows further details of the individual microelement 52, which has a "back wall" 62, a pair of "side walls" 60, a "front edge" at 64 on each of the side walls 60, and a base line 66 along the bottom of the side walls 60.

To penetrate the stratum corneum of skin, the microstructure or "patch" 50 is rubbed back and forth substantially along the direction designated by the letter "C" (which is a preferred, predetermined direction). In this manner, the edges at 64 will cut or lance through the skin cells to a predetermined penetration depth, which will be substantially equivalent to the protrusion distance of the microelements 52.

Figure 7:
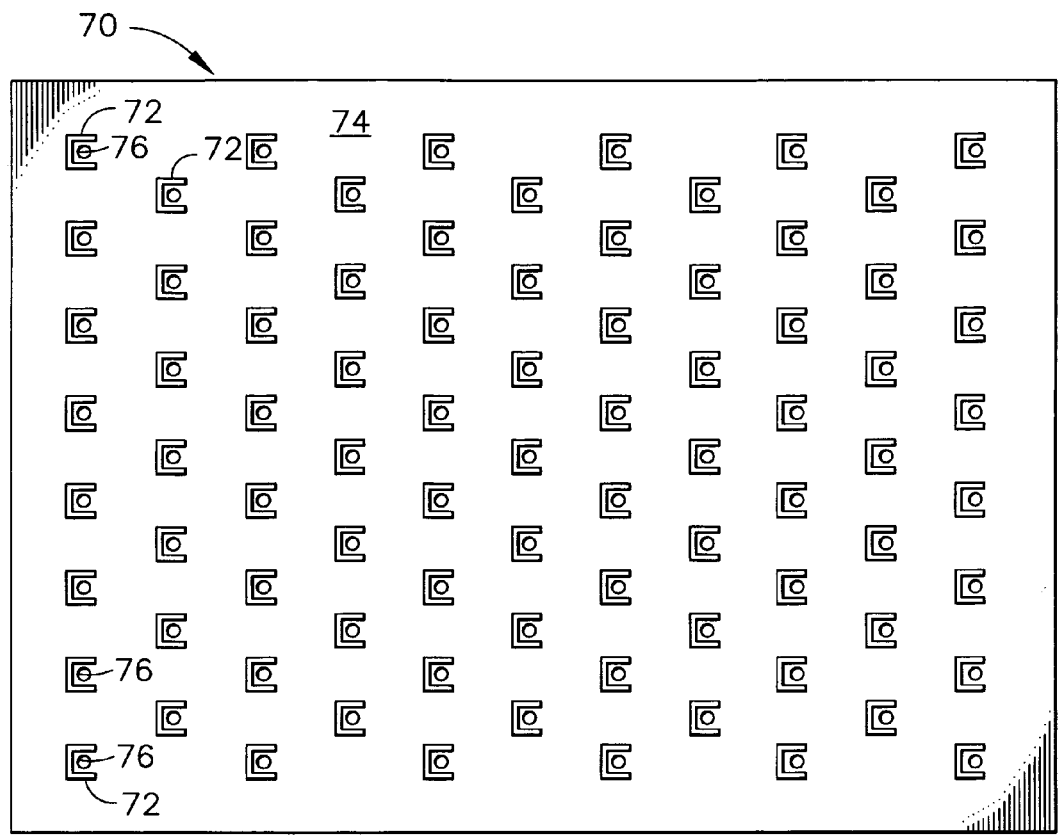
FIG. 7 is a plan view of an array of the cubic rectangular microelements of FIG. 5 with the addition of through-holes in the substrate.

FIG. 7 illustrates a similar array of microelements, designated by the reference numeral 70. Each individual microelement 72 has a similar appearance to the open box-like microelements 52 of FIGS. 5 and 6, however, a through-hole 76 has been added within the "cup-like" area of the microelement 72. These holes typically would run completely through the base or substrate 74, although they could instead extend only partially into the substrate to connect to some type of internal channels. In that manner, these holes could become (or connect to) passageways of any shape, diameter, or length.

Figure 8:
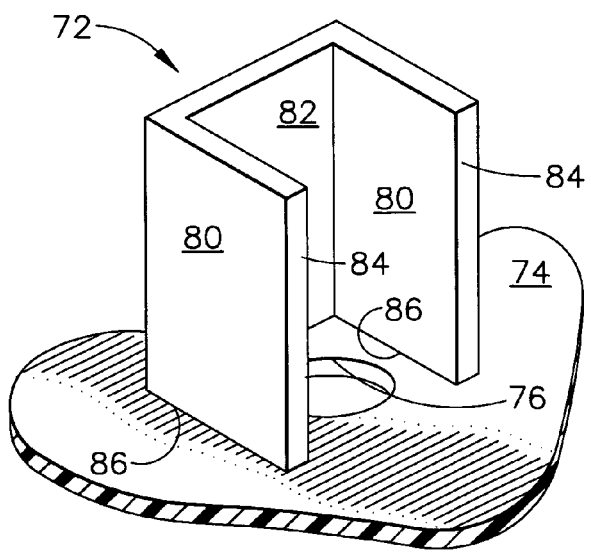
FIG. 8 is a perspective view of one of the cubic rectangular microelements of FIG. 7.

The microstructure array 70 could be formed into a "patch" that is applied to skin and rubbed in a back and forth manner substantially in the direction "C" indicated on FIG. 7 (which is a preferred, predetermined direction). FIG. 8 shows further details, in which there are two side walls 80, a back wall 82, two "front" edges 84, a base line 86 for each of the side walls 80, and the through-hole 76 that is proximal to the interior area of the microelement 72. In a similar manner to the previously described microstructure of FIGS. 3 and 4, the microstructure 70 disclosed on FIGS. 7 and 8 can be used to simultaneously penetrate the skin surface while delivering some type of active into the epidermis. Such systems can both penetrate the skin's outer layer and deliver to the epidermis in a single operation by a user.

Figure 9:
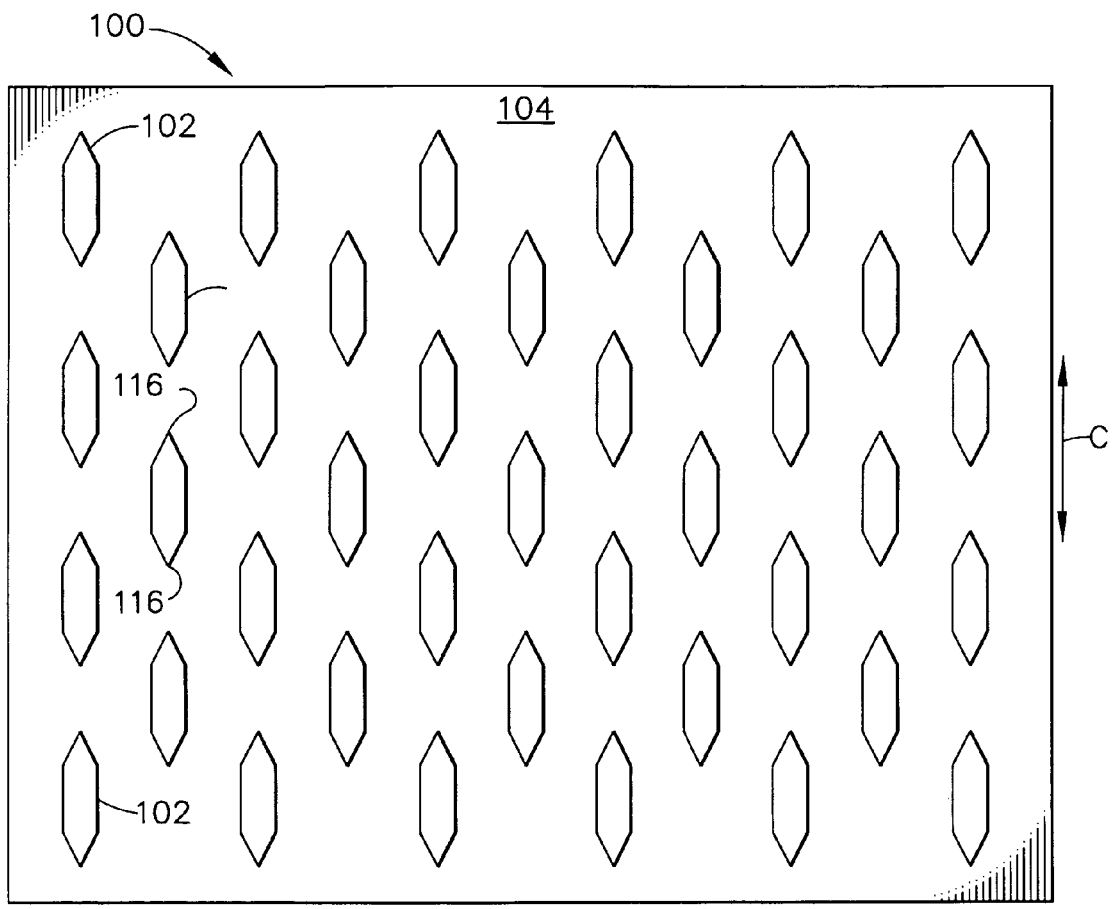
FIG. 9 is a plan view of an array of wedge-shaped microelements, as constructed according to the principles of the present invention.

FIG. 9 illustrates an array 100 of wedge-shaped microelements 102 mounted onto a base or substrate 104. As in some of the earlier-described embodiments, each column of microelements 102 can be offset from the adjacent column, as illustrated on FIG. 9. However, the columns could alternatively be made identical to one another, in which there would be no offset. A further alternative could arrange several columns with various offsets before the microelement pattern repeats, or the offsets could be substantially random so that there is no repetitive pattern.

Figure 10:
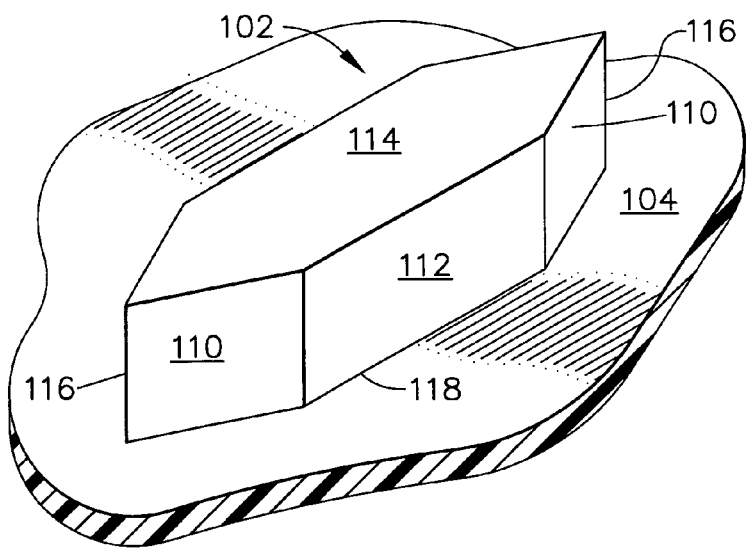
FIG. 10 is a perspective view of one of the wedge-shaped microelements of FIG. 9.

The wedge-shaped microelement 102 is illustrated in greater detail in the perspective view of FIG. 10. The top of the structure is at 114, and there are two elongated side walls 112 and a pair of converging side walls 110 that, at their line of convergence, form a cutting edge 116. There is also a base line 118 at the junction between the side wall 110 and the substrate 104.

The relatively sharp edge 116 is purposefully used to cut or slit (or "lance") the skin in the methodology described in this patent document. The overall wedge shape of the microelement 102 is provided as a more substantial structure than some of the other embodiments described herein. It also is probably easier to manufacture than the microelements described earlier, in FIGS. 1–8. In the microelements of the array 100 on FIG. 9, it is preferred to apply the array as a "patch" onto skin, and then rub it in a back and forth manner substantially along the line "C" (which is a preferred, predetermined direction). As can be seen from FIG. 9, the relatively sharp edges 116 will be used to cut into the skin when the patch 100 is moved in this manner along the line "C".

In essence, the edge 116 will tend to act as a miniature plow against the dead skin cells of the stratum corneum. A more descriptive view of the plowing action is provided in FIG. 27, which illustrates one of the "straight" wedge-shaped microelements 102 as it makes a slit or cut in the skin. The skin is depicted at 300, and it can be seen that the sharp edge 116 made up by the two converging faces 110 essentially plows through the top portions of the stratum corneum, starting at the point 302, and thereby parting the skin along the lines at 306. This leaves an inner portion of the skin temporarily exposed at 304.

Figure 27:
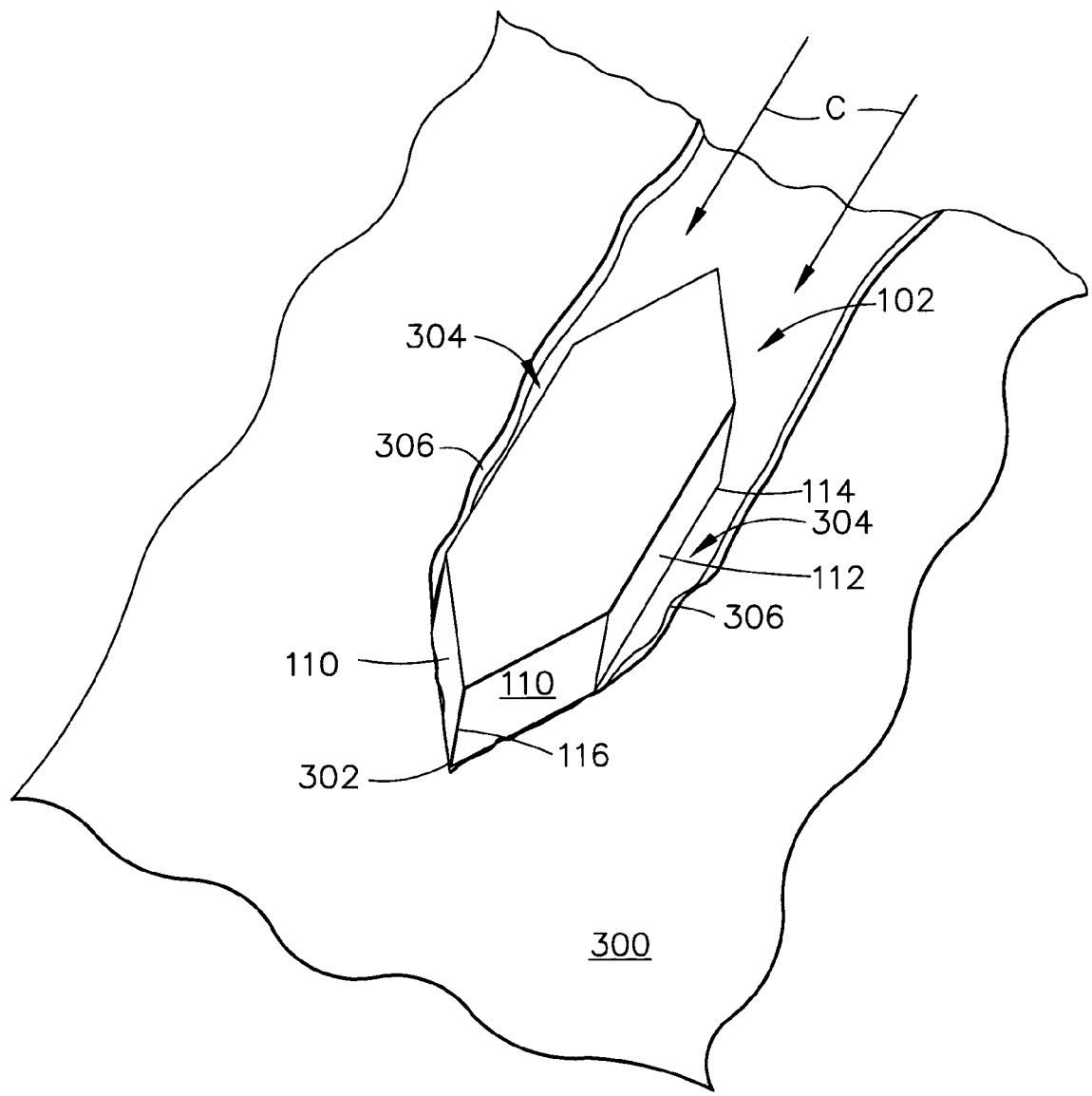
FIG. 27 is a perspective view of one of the "straight" wedge-shaped microelements 102 as it makes a slit or cut in skin.

On FIG. 27, the microelement 102 is being moved substantially in the direction of the arrows "C," thereby indicating that the skin is being cut in that direction. Of course, when the microelement 102 is moved in the opposite direction, it will tend to cut the skin in the opposite direction and form a new slit, or enlarge an existing slit.

It will be understood that various depths of the microelements and widths of the microelements can be constructed to increase or decrease the size and penetration depth of the slits made in the skin, and such dimension variations are envisioned by the inventors. Certainly, the exact shapes and sizes can be varied without departing from the principles of the present invention.

Figure 11:
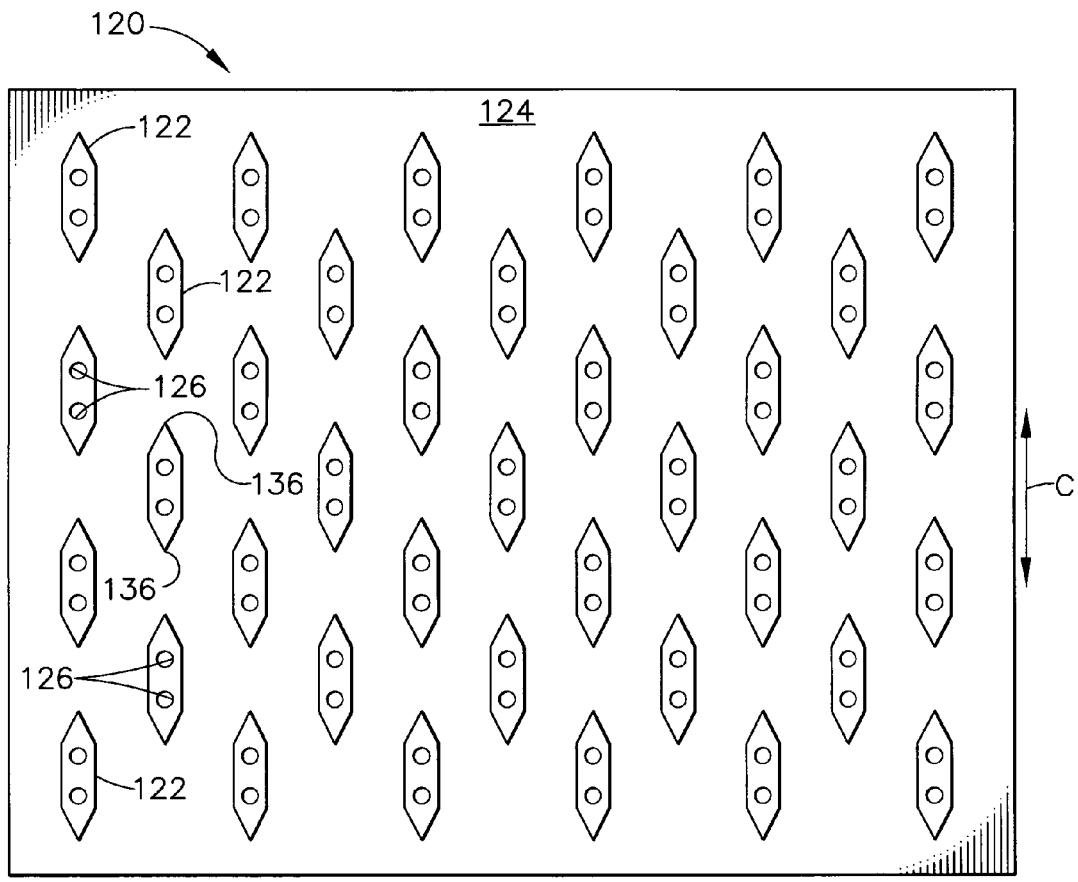
FIG. 11 is a plan view of an array of the wedge-shaped microelements of FIG. 9 with the addition of through-holes that penetrate through the microelement and through or into the substrate.

FIG. 11 shows a similar wedge-shaped microstructure array at 120, which has individual wedge-shaped microelements 122 that have two separate through-holes at 126. The microelements 122 are all mounted on a base or substrate 124. As viewed in FIG. 11, the columns of microelements 122 are somewhat different from one another, in that they are offset from one another in adjacent rows. This need not be the case, and alternatively the columns could be identical to one another to eliminate any offset, if desired. Again, alternatively there could be several columns with various offsets before the microelement pattern repeats, or the offsets could be substantially random so that there is no repetitive pattern.

Figure 12:
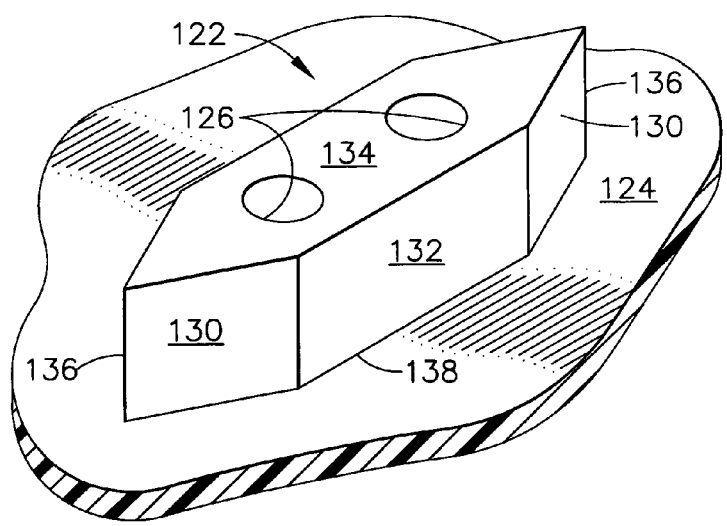
FIG. 12 is a perspective view of one of the wedge-shaped microelements having through-holes of FIG. 11.

FIG. 12 shows further details of the individual microelement 122, in which a top surface 134 and elongated side walls 132 are exhibited, along with converging side walls 130 that come to a sharp edge 136. A base line 138 is also illustrated as the junction between the microelement 122 and the substrate 124. The through-holes 126 are created to penetrate entirely through the microelement 122, and preferably will also penetrate entirely through the base 124, although the holes 126 can become passageways that do not entirely penetrate through the base or substrate, but instead connect to some type of perpendicular runs or passageways, if desired. Since there are two separate holes 126 per microelement 122, it is possible to simultaneously deliver two different actives (one per hole in a single microelement) in a single operation, if desired.

The microelements 122 are designed to perform both a skin penetration function and a delivery procedure in a single step. In this particular structure, it can almost be guaranteed that there will be a lack of build-up of dead skin and other foreign matter within the delivery holes or passageways 126. Even if some of this foreign matter or dead skin cells accumulates in these passageways 126, a capillary action may result and accomplish delivery of at least one active or drug through the passageways 126 and into at least the epidermal layer of the skin.

Figure 13:
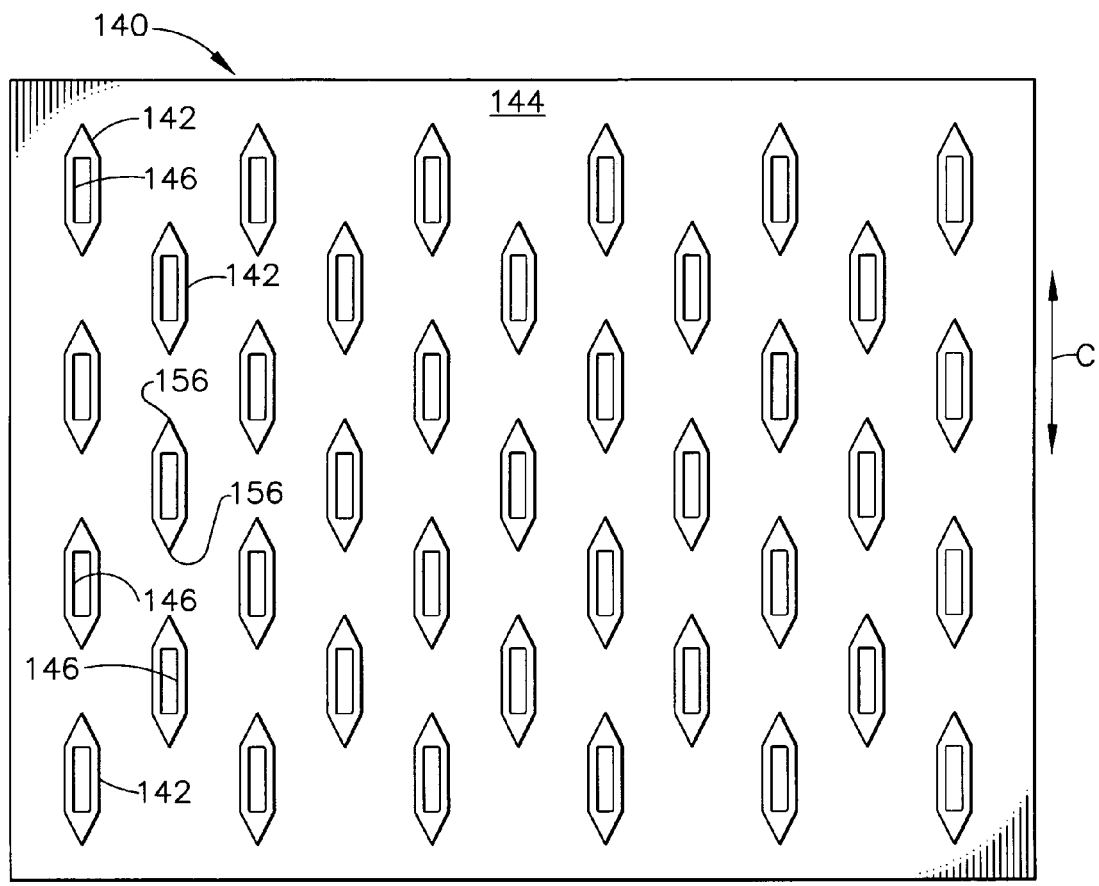
FIG. 13 is a plan view of an array of wedge-shaped microelements of FIG. 9, in which a through-slot is located in the microelements, which penetrates through or into the substrate.

FIG. 13 illustrates a microstructure array designated by the reference numeral 140 that contains a large number of individual wedge-shaped microelements 142 that are mounted to a base or substrate 144. These wedge-shaped microelements 142 contain a through-slot 146, through which at least one active or drug can be delivered through the outer skin surface just after the stratum corneum has been penetrated. In a similar manner to the structures of FIG. 11, the microelement array or patch 140 will preferably be placed on the skin surface and rubbed in a back and forth manner substantially along the direction "C" (which is a preferred, predetermined direction) to penetrate or cut skin cells of the stratum corneum.

Figure 14:
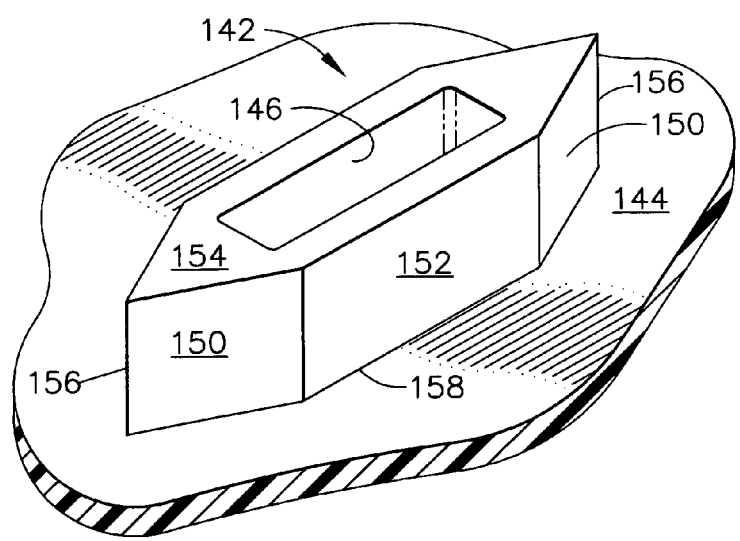
FIG. 14 is a perspective view of one of the wedge-shaped microelements having the through-slot of FIG. 13.

FIG. 14 shows greater details of an individual microelement 142, showing a top surface 154, side walls 152, converging side walls 150 that come to a relatively sharp edge 156, and a base line 158 where the microelement 142 adjoins the base or substrate 144.

The through-slot 146 can provide a larger cross-sectional area for delivery of at least one active or drug to the skin surface, as compared to the microelement 122 of FIG. 12. Of course, the actual dimensions of the microelement 142 could be either larger or smaller than similar microelements 122 illustrated on FIG. 12. Both sets of microelements 122 and 142 are relatively simple to construct, although the ones with the through-slot 146 may be somewhat easier to construct as compared to constructing multiple smaller through-holes 126.

The patch or array 140 can be used for a combinational step of skin penetration and delivery of at least one active, in a similar fashion to that described in some of the earlier embodiments. Other similar shapes of wedge-shaped structures could easily be constructed without departing from the principles of the present invention.

Figure 15:
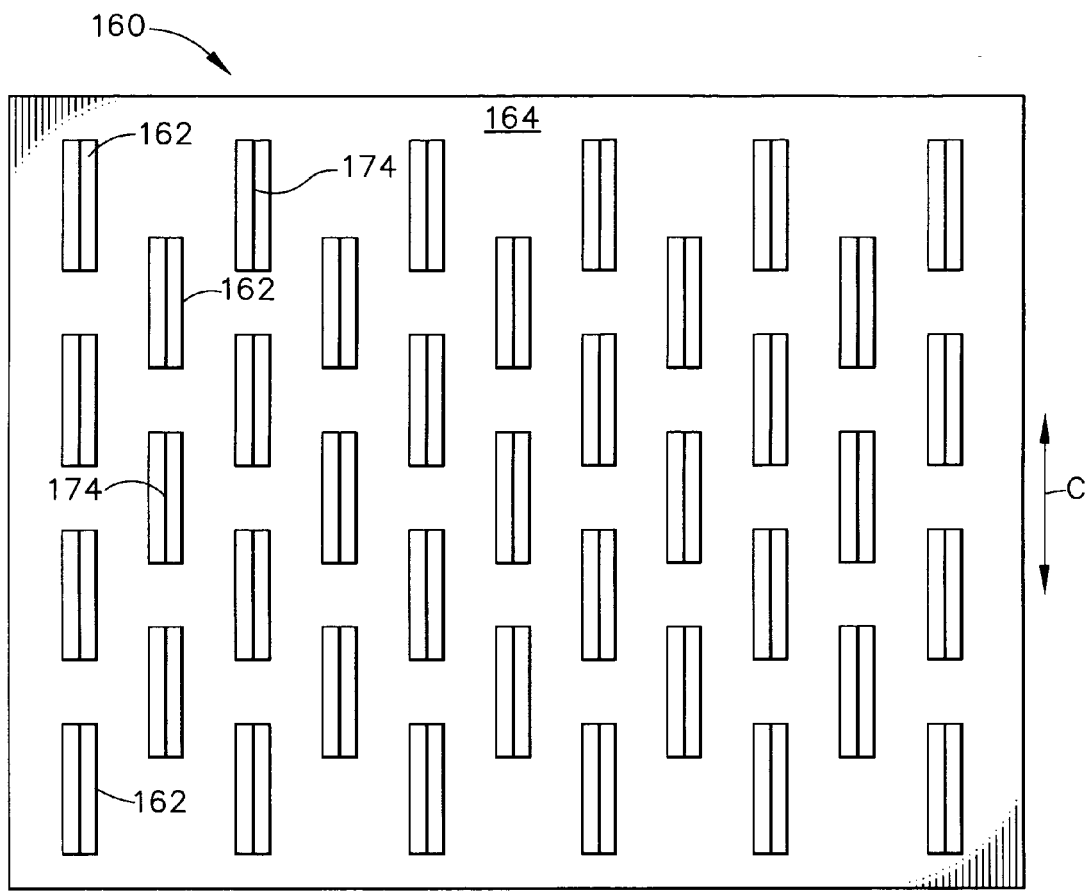
FIG. 15 is a plan view of an array of microelements having an elongated triangular shape, as constructed according to the principles of the present invention.
Figure 16:
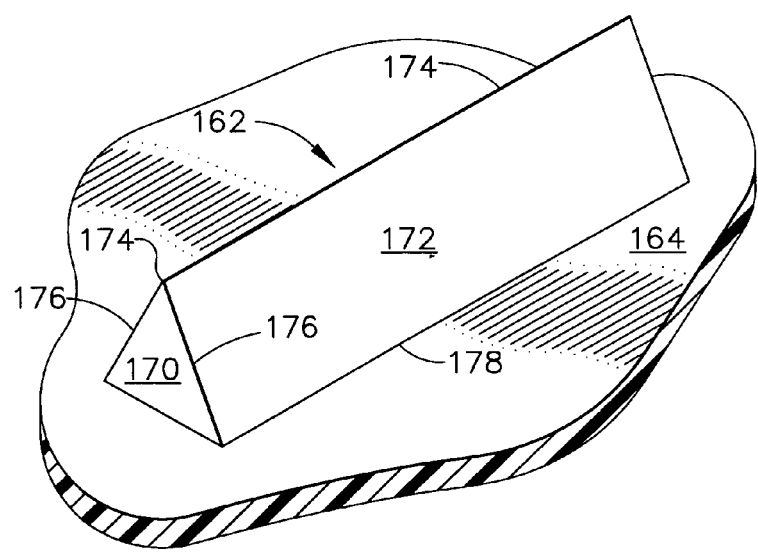
FIG. 16 is a perspective view of one of the elongated triangular microelements of FIG. 15.

FIG. 15 discloses an array or patch 160 of triangular-shaped wedge microelements 162, mounted on a base or substrate 164. As seen in FIG. 16, each of the microelements 162 consists of an elongated triangular shape, having a pair of triangular side walls 170, a pair of sloped elongated side walls 172, a top edge 174, and a pair of base lines 178. The junction between the triangular end walls 170 and the rectangular but sloped side walls 172 is designated at the reference numeral 176. The peak of the triangle is illustrated at 174, which is only one point along the top edge 174 of the microelement 162.

These triangular-shaped wedges can be useful in a skin penetration procedure, and preferably will be placed on skin in the form of a patch and then rubbed back and forth over the skin substantially in the direction "C" (which is a preferred, predetermined direction). The individual columns of microelements can be offset from one another in adjacent columns, as seen in FIG. 15. Alternatively, the columns could be identical to one another, without any offset. Another alternative could arrange several columns with various offsets before the microelement pattern repeats, or the offsets could be substantially random so that there is no repetitive pattern.

Figure 17:
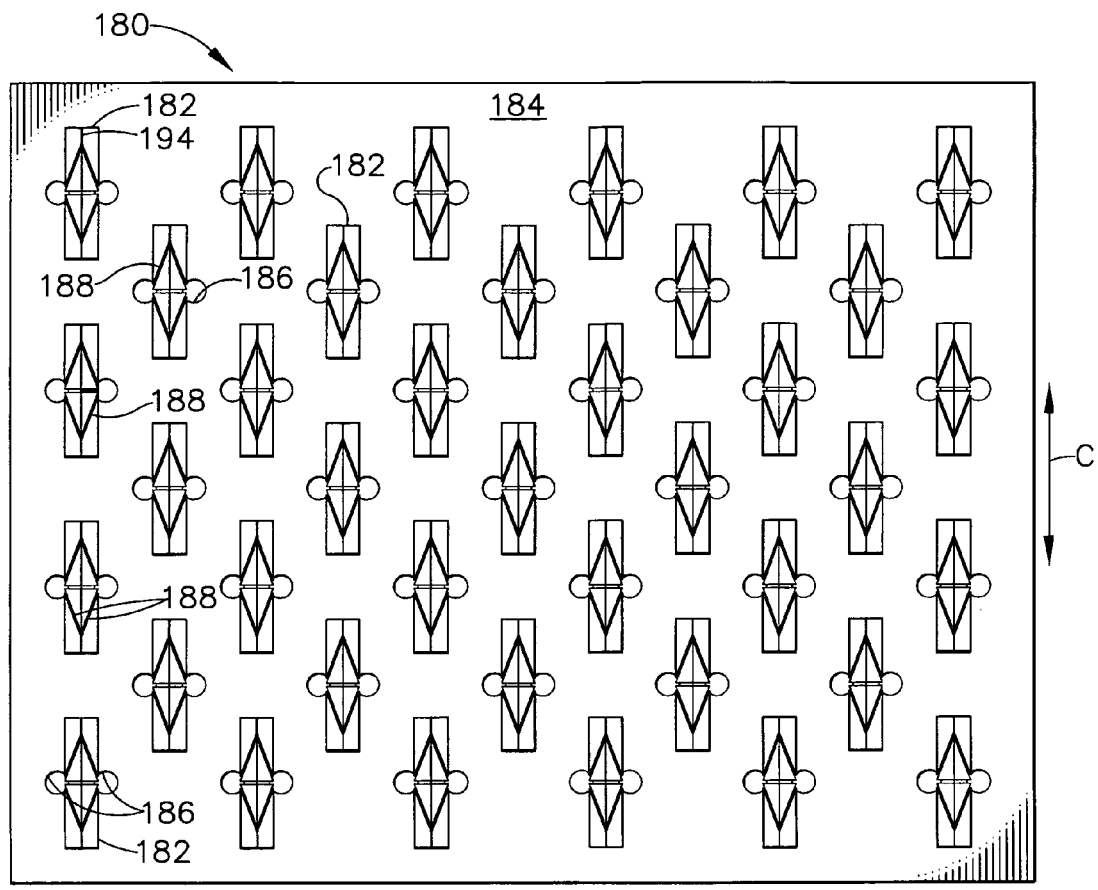
FIG. 17 is a plan view of an array of the elongated triangular microelements of FIG. 15 with the addition of through-holes in the substrate, and elongated channels along the surfaces of the triangular microelements.

FIG. 17 discloses a similar microelement array 180, which has triangular-shaped wedges as individual microelements 182 that are placed or are formed upon a base or substrate 184. In the "patch" 180, there are multiple through-holes 186 and channels 188 for placing at least one active through the stratum corneum.

Figure 18:
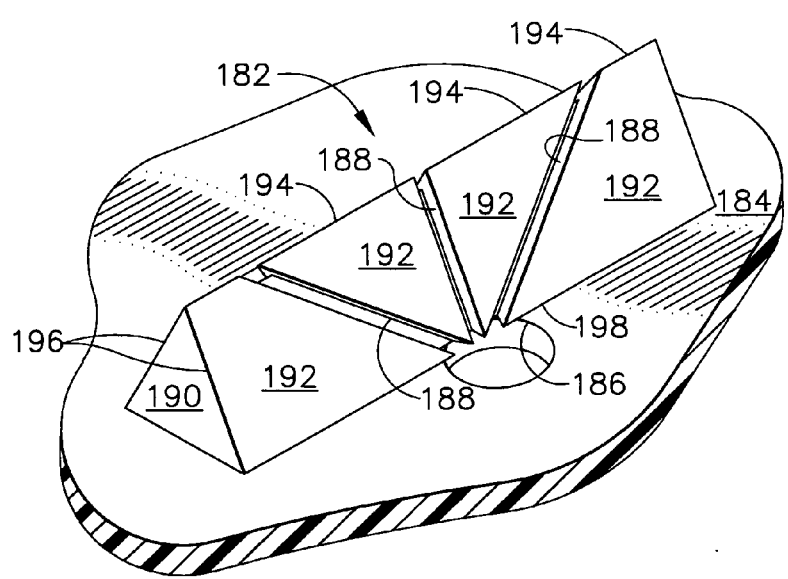
FIG. 18 is a perspective view of one of the elongated triangular microelements of FIG. 17.

FIG. 18 shows the channels 188 and holes 186 in a magnified view, in which the holes 186 would typically be designed to penetrate entirely through the substrate 184; however, such holes 186 could only partially penetrate the base if they connect to some other type of passageway within the base structure itself.

The triangular shape of the microelement 182 is seen on FIG. 18 along the side wall 190, which connects to sloped, rectangular side walls 192 along edges 196. A top edge 194 exists between the two triangular side walls 190, and a base line 198 marks the line between the microelement 182 and the substrate 184.

On FIG. 18, there are three separate channels 188 in the surface of the elongated side wall 192. Of course, fewer channels could be utilized, if desired, or even more numerous channels could be used. These channels 188 lend themselves well for capillary action to allow at least one active to flow through the holes 186 and along the channels 188 into the stratum corneum, even if the areas between the microelements 182 become substantially full of dead skin cells and other foreign substances.

The triangular wedge structures of both FIGS. 16 and 18 are basically designed to penetrate the stratum corneum layer of skin. This is accomplished by moving the microelement patches 160 or 180 in a back and forth manner substantially in the direction "C" as shown on FIGS. 15 and 17. Of course, if the microelement patches were to be moved in a different direction, particularly one that was perpendicular to the line "C" (which is a preferred, predetermined direction), then it is quite likely that the skin would not be cut and penetrated (at least not to the extent as compared to when the patch is used in the intended "C" direction). This has much usefulness, however, that concept is not part of the present invention. Instead, that type of methodology is disclosed in a companion patent application, Ser. No. 09/952,043 which is also assigned to The Procter & Gamble Company, and having the title "Microstructures for Treating and Conditioning Skin."

Figure 19:
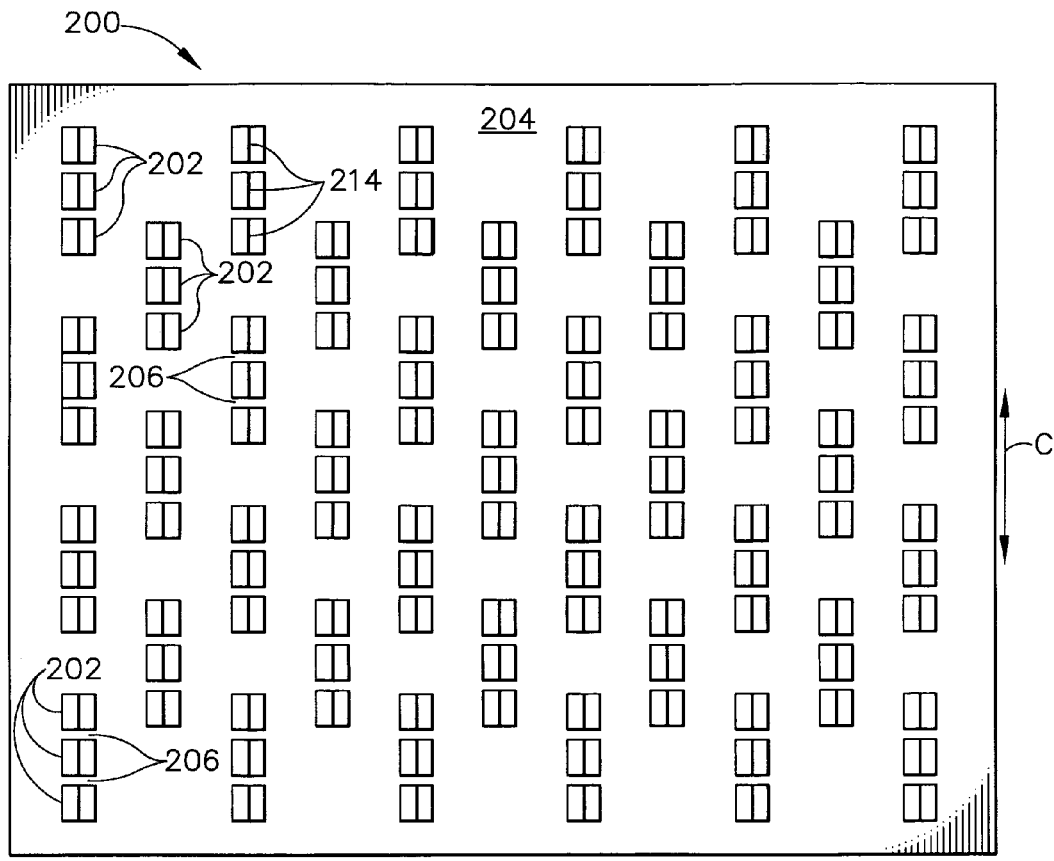
FIG. 19 is a plan view of an array of triangular-shaped wedge microelements that are grouped in closely-spaced arrangements, as constructed according to the principles of the present invention.
Figure 20:
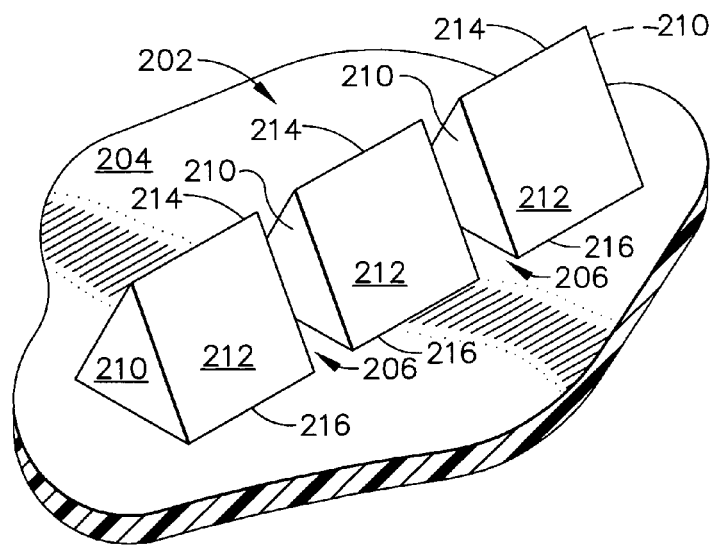
FIG. 20 is a perspective view of one of the closely-spaced triangular wedge microelements of FIG. 19.

Another refinement of the triangular-shaped wedge is illustrated on FIGS. 19 and 20. On FIG. 19, a microstructure array or patch 200 is illustrated as containing multiple wedge-shaped microelements 202 that are placed upon, or are formed thereon, a base or substrate 204. As seen in FIG. 20, each of the microelements 202 is comprised of three separate triangular-shaped wedges, each having a space therebetween at 206.

On FIG. 20, it can be seen that the three sections of the triangular-shaped wedge 202 includes a triangular-shaped side wall 210, a pair of rectangular, sloped side walls 212, a top edge 214, and a base line at 216 where the microelement 202 joins the substrate 204. Each of the three wedge shapes is separated by a space 206, in which a center triangular wedge shape is surrounded on both sides by a second, outer similar wedge shape, and spaced apart from each of these outer wedge shapes by the spacing area 206.

The three separate wedge shape of microelement 202 (which are separated by the spaces 206) provide more individual cutting edges 214. Each peak of a triangular end wall 210 represents a new cutting or "plowing" point when the patch 200 is moved substantially along the line "C".

The preferred use of the array or patch 200 is to apply the patch directly to the skin, and then rub the patch in a back and forth manner along the skin surface substantially in the direction "C" as seen on FIG. 19 (which is a preferred, predetermined direction). This particular design penetrates the skin outer layers quite well, but is not designed to also apply an active at the same time. Of course, through-holes and channels could be added to this structure, if desired, although that type of structure would probably be easier to construct when using the shape disclosed in FIG. 18 for the microelement 182.

It will be understood that a microelement patch could be composed of any one shape of microelements, or could be comprised of several different shapes on a single substrate or patch structure, without departing from the principles of the present invention. Moreover, it will be understood that the microelements disclosed herein could be of all the same height, or of different heights on the same substrate or patch, without departing from the principles of the present invention. Finally, it will be understood that minor modifications to the shapes disclosed in the drawings are contemplated by the inventors, and would still fall within the principles of the present invention.

It will also be understood that the microelement arrays or patches that contain through-holes or through-slots need not have such through-holes or through-slots for each and every one of the individual microelements that make up the array. In other words, the passageways that flow through the microelements (or adjacent thereto) could be constructed on only one-half of the microelements, if desired, while still achieving most of the results that would otherwise be achieved if such through-holes or through-slots were found at each of the microelements. Certainly, the holes or slots could be varied in size or diameter to either reduce or increase the amount of fluidic material that flows therethrough. All of these variations are contemplated by the inventors, and would fall within the principles of the present invention.

In general, the microelements of the present invention described above are longer than those used only for exfoliation, and the lengths of the microelements would typically be in the range of 50–1000 microns. This will allow the microelements to penetrate the stratum corneum. As noted above, on FIGS. 1, 3, and 21, the direction of sliding the patch is not important; however, on FIGS. 5, 7, 9, 11, 13, 15, 17, and 19, the direction of sliding is more important, and should be substantially in the direction as depicted by the arrow "C." This will allow the microelements to cut the skin, and to penetrate the skin to a depth that will pierce the stratum corneum to a certain extent. This will allow an active or other type of fluidic material or fluidic compound (such as a liquid or a cream) to penetrate much more easily through the stratum corneum.

Figure 21:
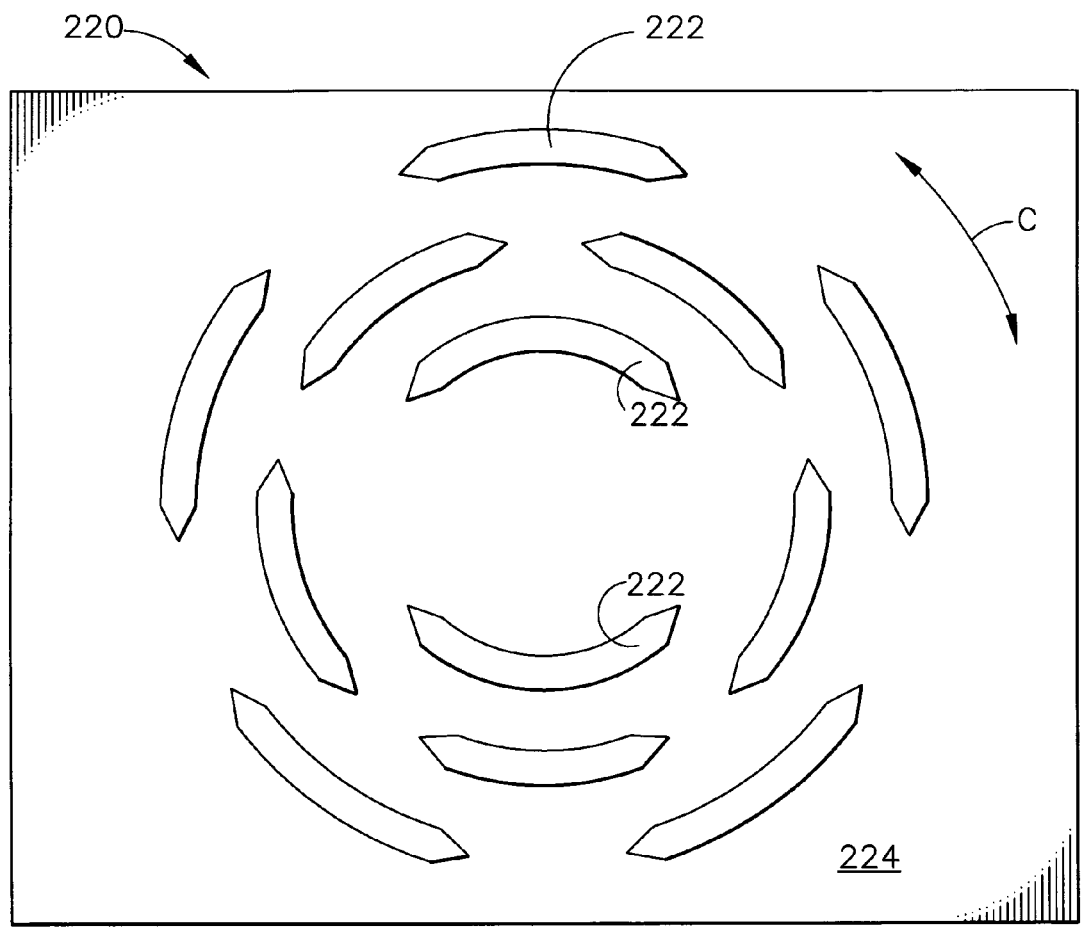
FIG. 21 is a plan view of an array of arcuate-shaped microelements with wedged tips, as constructed according to the principles of the present invention.
Figure 22:
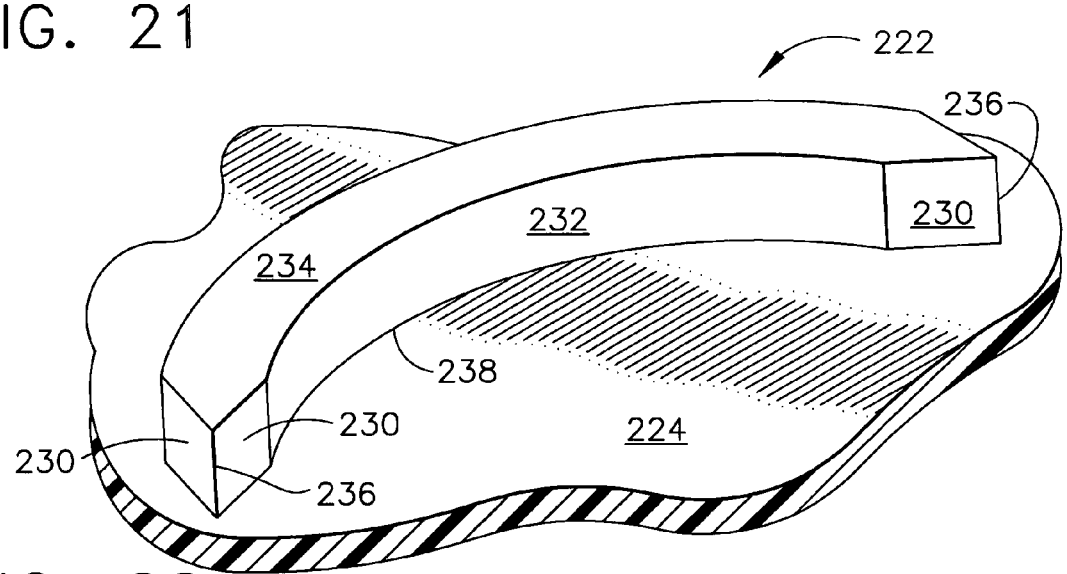
FIG. 22 is a perspective view of one of the wedge, arcuate-shaped microelements of FIG. 21.

FIG. 21 illustrates a "coiled appendage" of a sort, in which multiple curved wedge-shaped microelements at 222 are placed on a substrate 224 to form an array or patch generally designated by the reference numeral 220. FIG. 22 illustrates one of these arcuate microelements 222 in greater detail. The microelement 222 includes two wedge-shaped points that are made up of relatively flat surfaces 230 that converge at an edge 236. The two wedge-shaped "cutting surfaces" at the edges 236 are joined by a curved body that has side walls 232, a top surface 234, and a base "line" at 238 that is curved or arcuate in shape.

The array or patch 220 is used by placing the patch on the surface of skin, and then rotating the patch substantially along the arc designated at the letter "C." This will tend to slit or otherwise cut the skin along the relatively sharp edges 236 in either direction of the curved microelements 222.

The curved microelements 222 on the array/patch 220 can be used in two methodologies: (1) the skin is first cut, the patch 220 removed, and then a fluidic compound (e.g., a liquid material or cream) is applied to the skin; (2) the fluidic compound is applied first to the skin, then the array/patch 220 is pressed down on the same area of the skin and rotated to create the openings, thereby allowing the fluidic compound to penetrate more easily through the stratum corneum.

Figure 23:
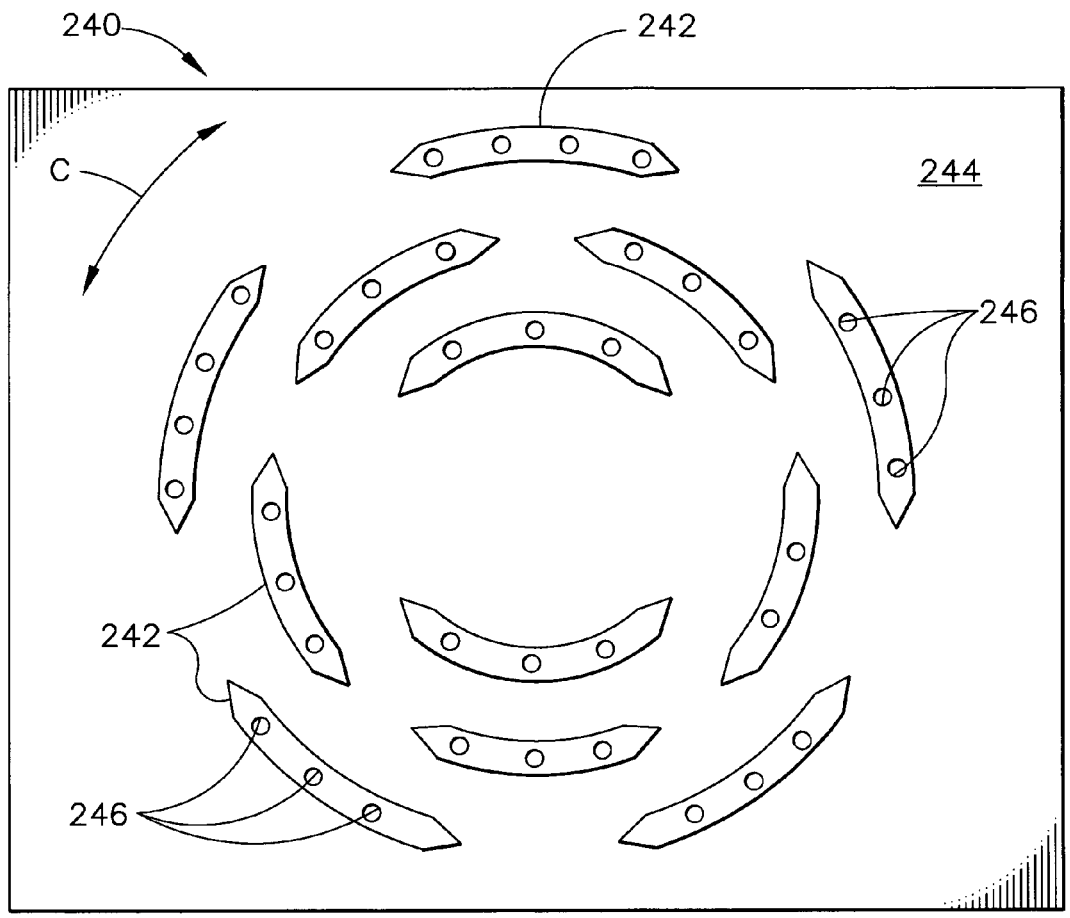
FIG. 23 is a plan view of an array of the wedge, arcuate-shaped microelements of FIG. 21 with the addition of through-holes that penetrate through the microelement and through or into the substrate.

A similar arcuate or curved wedge structure is illustrated in FIG. 23, in which the individual microelements at 242 are placed upon a substrate 244 to make up an array or patch 240. These curved wedges also may be referred to as "coiled" structures. One of the microelements 242 is illustrated in greater detail in FIG. 24, and it can be seen that through-holes 246 are placed through the top surface 254 of the microelement 242. This will allow a fluidic compound to pass through the holes 246 and into the skin after the stratum corneum has been slit or otherwise pierced by the arcuate microelements 242. Each curved microelement 242 exhibits a pair of sharp edges at 256 that are made up by relatively flat sides 250 that converge along the line 256. The curved structure has side walls 252, a top surface 254, and a base "line" or arc at 258 where the microelement 242 joins the substrate 244.

Figure 24:
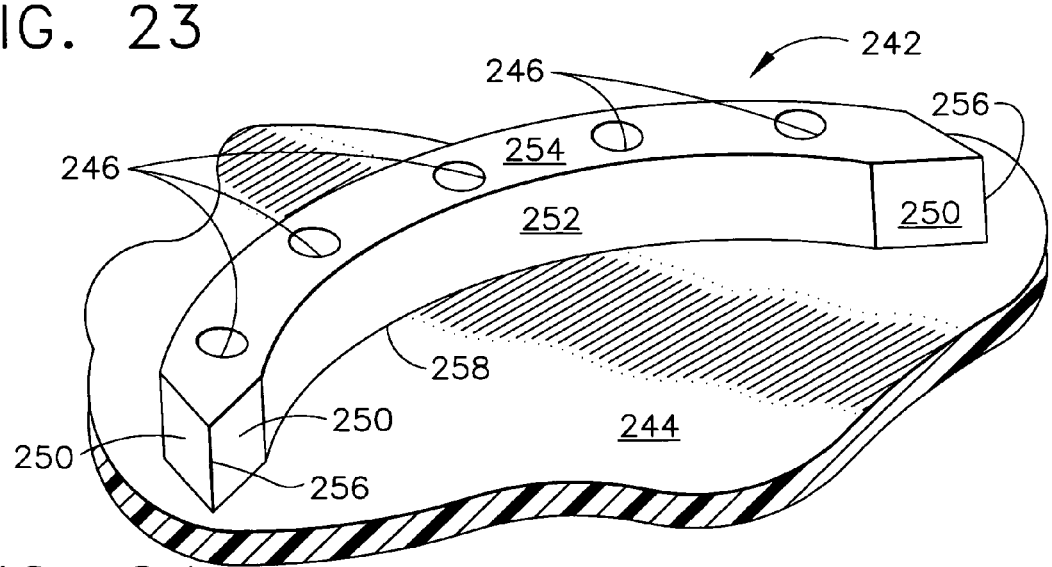
FIG. 24 is a perspective view of one of the wedge, arcuate-shaped microelements of FIG. 23 having through-holes.

In the structures of FIGS. 23 and 24, the patch 240 would typically be placed upon the skin surface and then rotated substantially in the direction designated by the curve "C." The fluidic compound that is to penetrate through the stratum corneum is already contained within some type of reservoir or chamber (or perhaps a non-woven impregnated material) that will then seep through the holes 246, including by capillary action.

Figure 25:
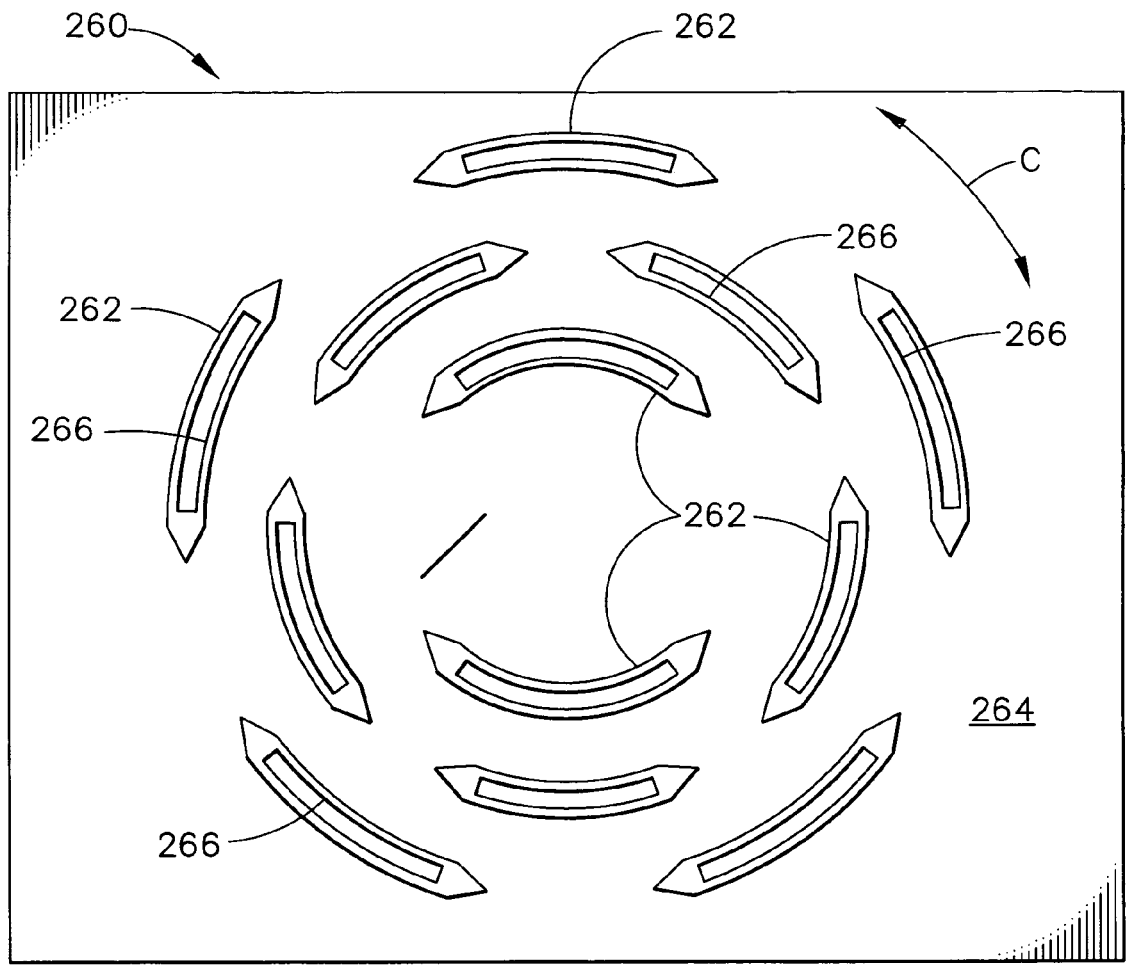
FIG. 25 is a plan view of an array of the wedge, arcuate-shaped microelements of FIG. 21 in which a through-slot is located in the microelements, which penetrates through or into the substrate.
Figure 26:
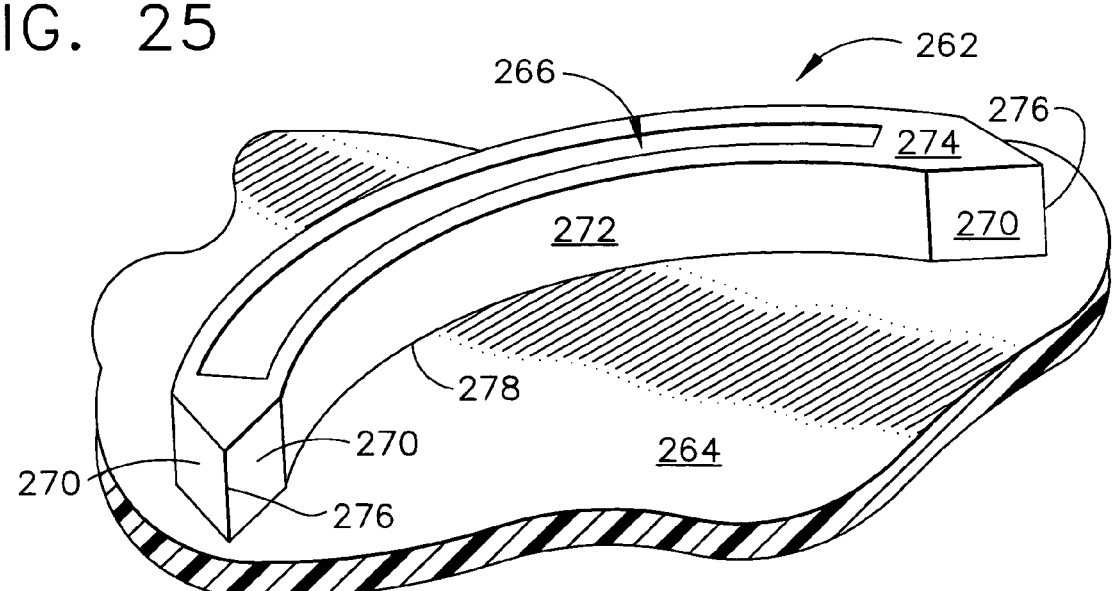
FIG. 26 is a perspective view of one of the wedge, arcuate-shaped microelements of FIG. 25 having the through-slot.

An alternative structure is illustrated in FIG. 25, in which the curved microelements 262 exhibit through-slots at 266 that are also arcuate in shape. The curved microelements 262 are placed upon a substrate 264, and the overall structure makes up an array or patch 260. FIG. 26 shows the individual microelement 262 in greater detail, and illustrates the sharp edges at two of the ends of the curved microelement at 276, which are made up of converging side walls 270. A curved side wall 272 is illustrated, along with a top surface 274 and a base "line" or arc at 278 where the microelement 262 joins the substrate 264. The through-slot 266 is easily visible in FIG. 26.

The arcuate microelement 262 is used in a similar manner to that illustrated in FIG. 24, in which the array/patch 260 is placed upon skin and rotated substantially along the arc "C," and then a fluidic compound is allowed to pass through the slot 266 through the stratum corneum, as desired.

Figure 28:
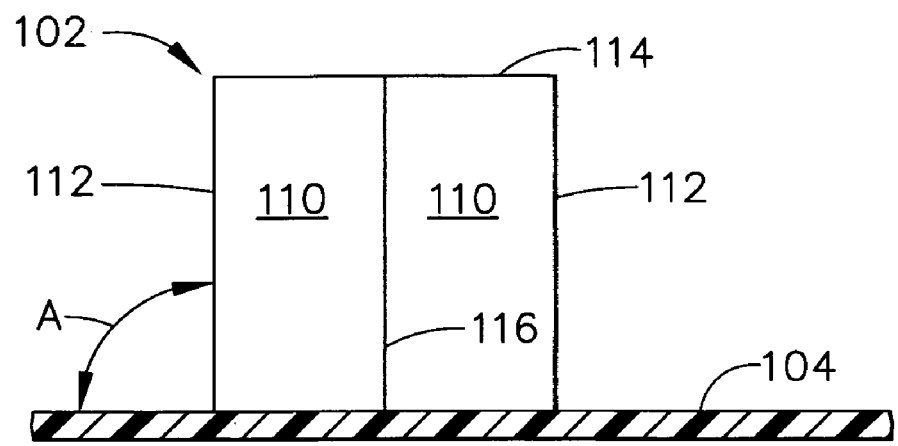
FIG. 28 is an elevational view in partial cross-section of a wedge-shaped microelement of FIG. 10, in which the side walls are perpendicular with respect to the substrate plane.

FIG. 28 illustrates the wedge-shaped microelement 102 from its "sharp" end in an elevational view. The two converging sides 110 are seen to form a relatively sharp edge at 116, which travels vertically from the top of the substrate/base 104 to the top surface 114 of the microelement 102. The angle "A" between the substrate top surface at 104 and the side wall 112 is clearly visible. On FIG. 28, this angle "A" is approximately 90°, and therefore forms a perpendicular angle.

Figure 29:
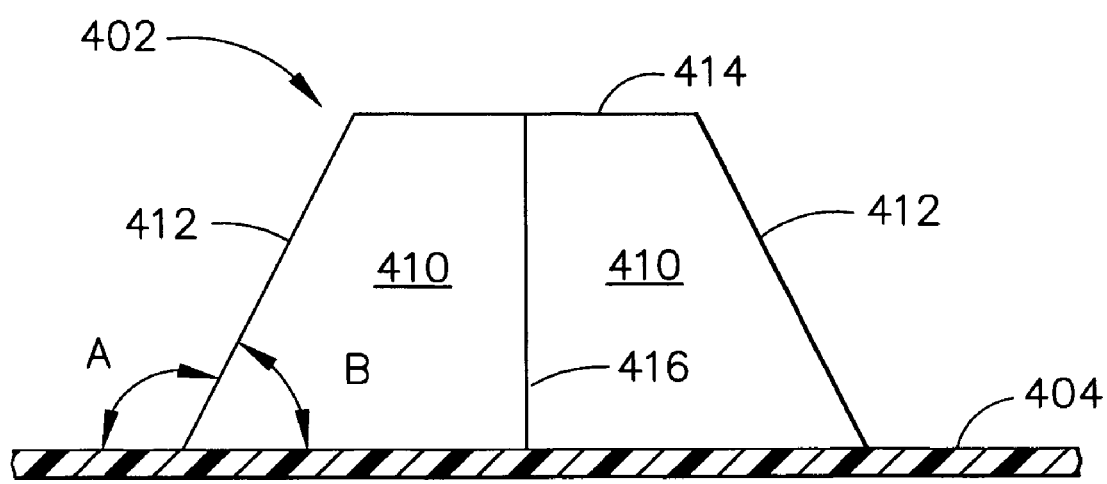
FIG. 29 is an elevational view in partial cross-section of a wedge-shaped microelement similar to that of FIG. 10, in which the side walls have an angular relationship that is not perpendicular with respect to the substrate plane.

FIG. 29 shows an alternative shape for a wedge-shaped microelement designated by the reference numeral 402. This wedge-shaped microelement has a similar appearance from above to that of the wedge-shaped microelement 102, except that its elongated side walls are not formed by a perpendicular angle to the substrate.

On FIG. 29, the substrate 404 is joined to the outer wall that is elongated along the side of the microelement (i.e., the wall 412) by an angle "A" that is greater than 90°. Its complimentary angle is illustrated at "B." Angle B is between 45° and 60° in FIG. 29, but of course could be any angle that will successfully operate to penetrate the skin.

The front walls that converge are illustrated at 410, and converge along the relatively sharp edge at 416. This non-perpendicular wall shape of a microelement 402 may have some advantages with regard to manufacturing and with regard to overall strength of the structure.

Figure 30:
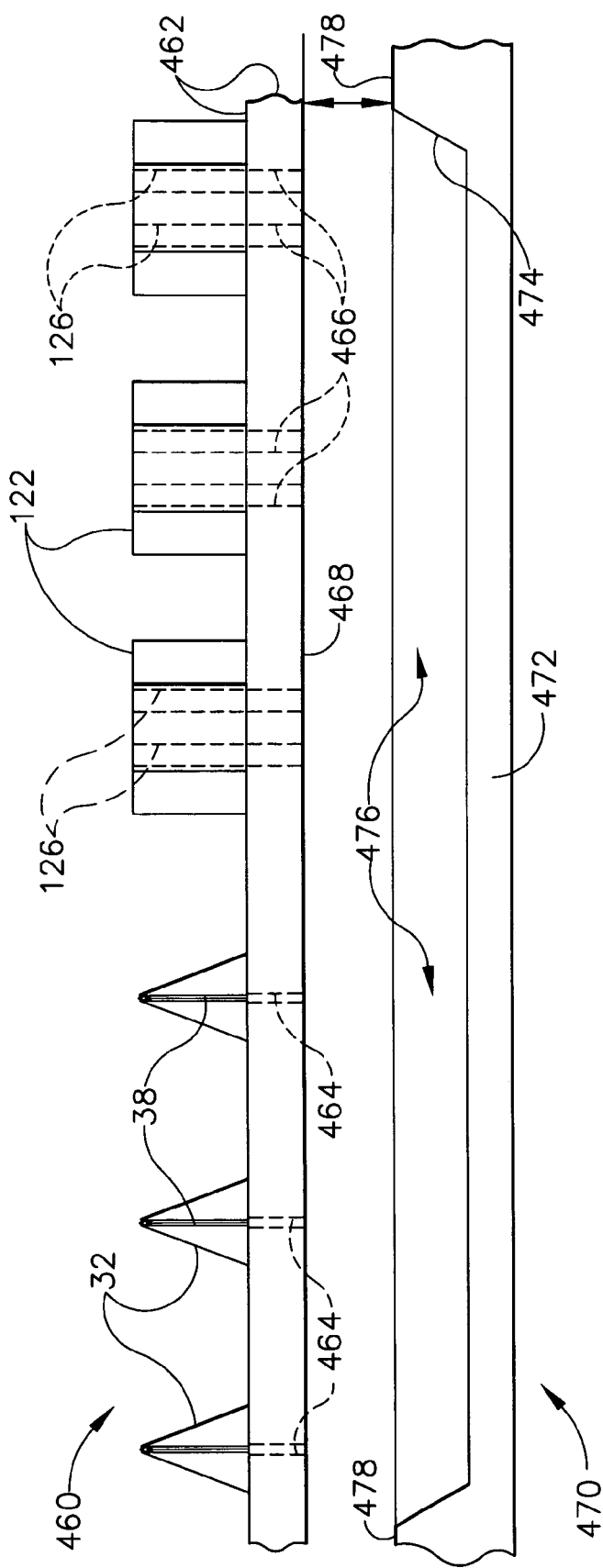
FIG. 30 is an elevational view in partial cross-section of an array of microelements similar to those found in FIG. 23, with the addition of through-holes or passageways to a reservoir structure below the main substrate.

FIG. 30 is a side elevational view in partial cross-section of a microstructure that contains an array of different shaped microelements and a corresponding substrate, designated at the reference numeral 460, as well as an underlying reservoir structure designated by the reference numeral 470. On FIG. 30, the array of microelements 460 is illustrated as having a set of pyramidal microelements 32 having grooves or channels 38 along the sides of the pyramid shapes, and a set of wedge-shaped microelements 122 having through-holes 126. The base or substrate is designated at the reference numeral 462.

On FIG. 30, the through-holes actually travel all the way through both the microelements and the substrate 462 to form passageways, and these passageways are depicted in two groups. The first group is a combination of the grooves or channels 38 in the pyramidal microelements 32 that are connected to the through-holes 464, to form a common set of passageways that extend from the bottom surface of the base or substrate 462 through the top surface of this substrate 462 and are in communication with the channels or grooves 38. The second set of passageways comprises a set of through-holes 466 that are in communication with the microelement through-holes 126 of the wedge-shaped microelements 122. These through-holes 126 and 466 must be in registration with one another to form complete passageways from the top of the microelement 122 to the bottom of the substrate of 462. Naturally, there could be some horizontal runs that connect similar passageways, if desired.

The bottom portion 470 depicted in FIG. 30 includes a reservoir structure that has a bottom wall at 472 and a reservoir area or volume at 476 that is bounded by the side walls of the reservoir at 474. Multiple such compartments or chambers can be constructed to house multiple actives. The upper portion of this reservoir structure 470 would typically be planar, as depicted at the reference numeral 478, and would make contact against the bottom surface at 468 of the microstructure/substrate apparatus at 460. It is important that the reservoir 476 be in communication hydraulically or pneumatically with the passageways 464 and 466, thereby allowing a fluidic drug or other active to reside within the reservoir confines at 476 until used, and then for the fluidic drug or active to be directed through the passageways 464 and 466 to the upper surface of the microelements 32 and 122.

Figure 31:
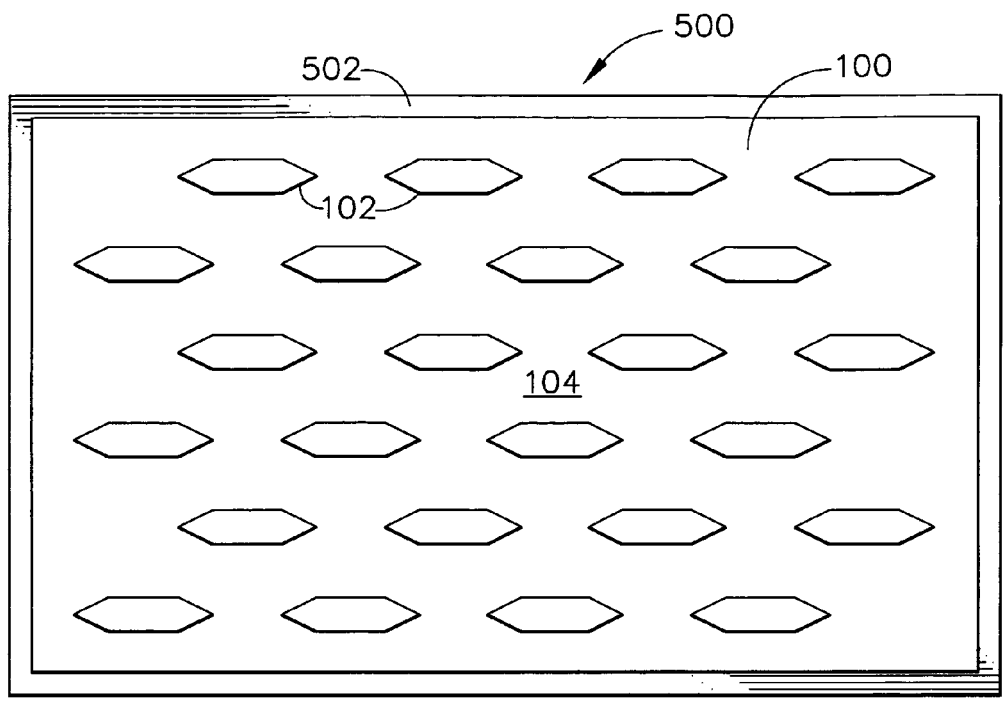
FIG. 31 is a plan view of a microelement array as seen in FIG. 10, with the addition of a non-woven backing material that is laminated to the original substrate.

FIG. 31 illustrates an array of wedge-shaped microelements 102 on a substrate 104 that makes up a microstructure apparatus designated by the reference numeral 100. Microstructure apparatus 100 comprises a top layer that is laminated to a non-woven backing 502, which is preferably thin enough so as to be substantially flexible. This overall structure is generally designated by the reference numeral 500 on FIG. 31.

The top layer 100 that contains the multiple microelements 102 can have as a substrate and microelement material some type of moldable plastic, such as nylon, or a polycarbide material, or PMMA, for example (and these materials may be used with any microelement shape). The bottom or backing material 502 preferably is a substantially flexible material that exhibits a soft texture. Typically a non-woven material gives an impression of cloth, and thus can provide the desired soft texture.

The non-woven backing material 502 can be laminated with the microelement layer 100 by use of a chemical glue or a heat-activated adhesive, for example. On FIG. 31, the non-woven backing is somewhat larger in length and width than the microelement layer 100, and thus can be seen along the edges.

Figure 32:
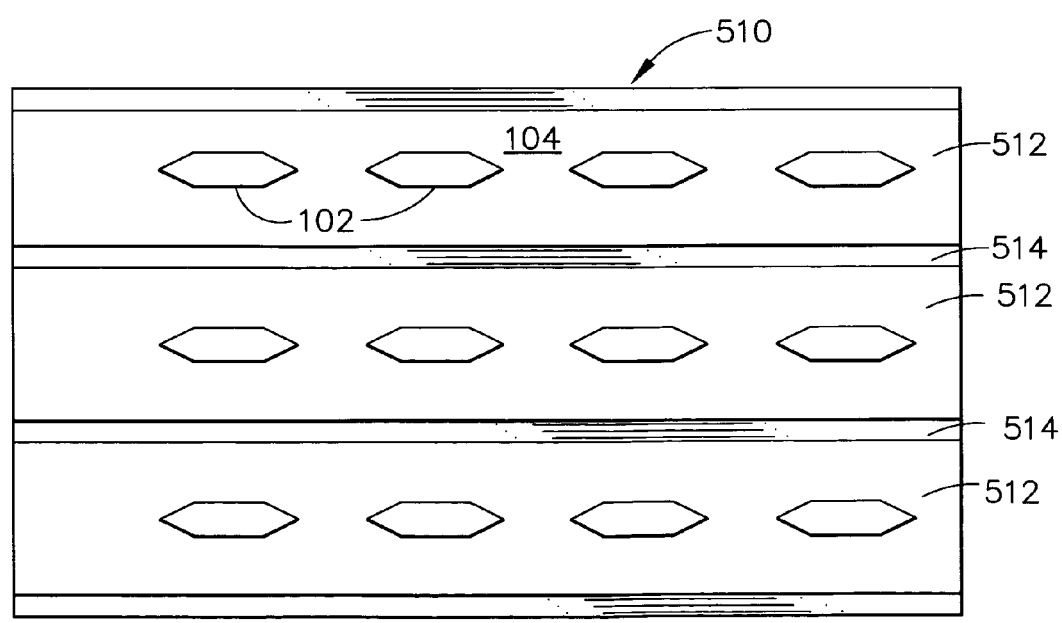
FIG. 32 is a plan view of a plurality of microelement strips that are laminated onto a non-woven backing.

FIG. 32 illustrates a similar laminated structure, however, the microelements 102 are formed as strips 512, in which there are several such strips that contain rows of the microelements. The non-woven backing material can be seen both along the top and bottom edges, and also between the strips at 514 on FIG. 32. The overall structure is generally designated by the reference numeral 510.

Figure 33:
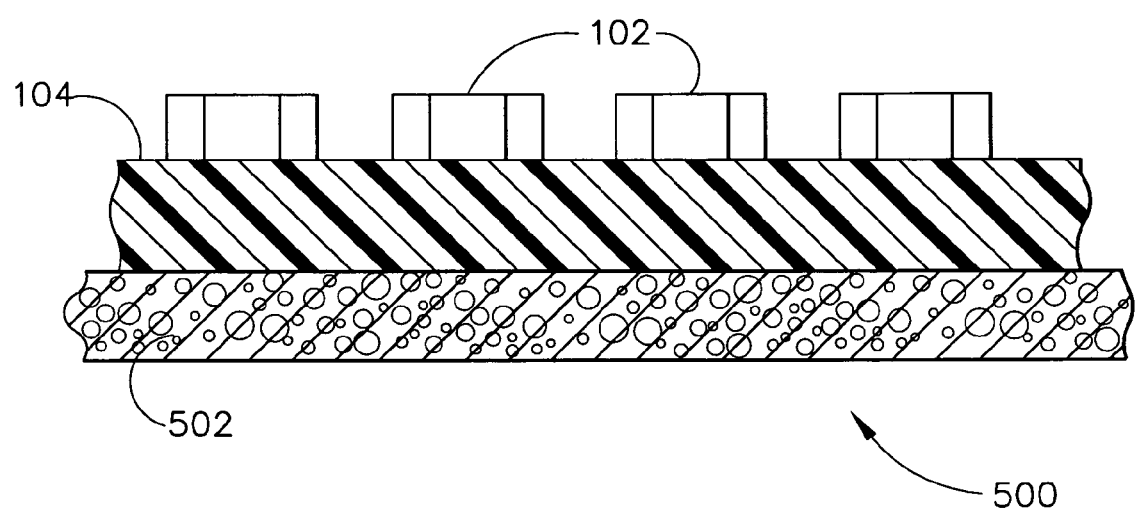
FIG. 33 is an elevational view in partial cross-section of a microelement array as seen in FIG. 10, showing further details of the substrate and non-woven backing.

In FIG. 33, the microelements 102 are visible at the top, as residing above the substrate 104. The bottom portion of the substrate is permanently affixed to the non-woven backing material 502, thus leading to the overall structure at 500.

As discussed above, the fixing of the non-woven backing material 502 to the substrate 104 can be by some type of adhesive used in lamination, or perhaps using a sonic bonding process. Alternatively, a co-extruded material could be used.

One major advantage to using a non-woven backing material as depicted in FIGS. 31–33 is that this non-woven material 502 (or 514 on FIG. 32) can be impregnated with at least one active, and thereby effectively become a "reservoir" without creating an actual chamber having an open volumetric space. This not only saves a manufacturing procedure step by not requiring a true open chamber to be constructed, but also allows the overall structure of the "patch" shown in the earlier figures to be made of a substantially flexible material that is much less likely to exhibit breakage problems.

It will be understood that various shapes of microelements can be used with the non-woven backing material, and various shapes of substrates can be laminated or otherwise affixed to the non-woven backing material. It will also be understood that the backing material may or may not be impregnated, all without departing from the principles of the present invention. Finally, it will also be understood that other suitable materials besides non-woven materials could be used for the backing at 502 and 514 on FIGS. 31 and 32, all without departing from the principles of the present invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A microstructure apparatus, comprising: a substrate, said substrate comprising a first surface and a second surface opposed thereto; and a plurality of non-rigid microelements affixed upon said first surface of said substrate and extending outwardly therefrom; said plurality of microelements being of predetermined sizes and shapes and so designed to make multiple slits or cuts in a stratum corneum layer of skin, when said microstructure apparatus is placed upon said skin and moved in at least one predetermined direction, wherein said at least one predetermined direction is in a direction that is substantially parallel to a surface of said skin, said apparatus further comprising a nonwoven absorbent backing layer mounted on said second surface of said substrate, said absorbent backing layer being impregnated with at least one fluidic compound and thereby acting as a fluid reservoir for use with said substrate, at least one of said substrate and said microelements having passageways therethrough, said passageways allowing for said fluidic compound to flow with efficiency from said backing layer to said surface of said skin when said apparatus is moved in at least one predetermined direction substantially parallel to a surface of said skin.

2. The microstructure apparatus as recited in claim 1, wherein a shape of said plurality of microelements exhibits a directional orientation, such that said directional orientation facilitates the penetration of the skin when movement of the microstructure apparatus occurs in said at least one predetermined direction.

3. The micro structure apparatus as recited in claim 2, wherein said predetermined direction is one of: (a) linear, or (b) arcuate.

4. The microstructure apparatus as recited in claim 1, wherein a shape of said plurality of microelements comprises one of: (a) a pyramid; or (b) an open, topless box having three walls; or (c) a longitudinal wedge; or (d) a curved wedge; or (e) an elongated triangle; or (f) a segmented elongated triangle.

5. The microstructure apparatus as recited in claim 1, wherein a shape of at least some of said plurality of microelements and their adjacent substrate comprises plural shapes, at least one said shape being selected from the group consisting of:

(a) a pyramid having at least one channel along a wall of said pyramid, and at least one passageway in said substrate proximal to the wall of said pyramid; said channel being in fluidic communication with said passageway; or (b) an open, topless box having three walls, and at least one passageway in said substrate proximal to one of said three walls; or (c) a longitudinal wedge having at least one passageway therethrough which is in fluidic communication with at least one other passageway in said substrate; or (d) a curved wedge having at least one passageway therethrough which is in fluidic communication with at least one other passageway in said substrate; or (e) an elongated triangle having at least one channel along a wall of said elongated triangle, and at least one passageway in said substrate proximal to the wall of said elongated triangle, said channel being in fluidic communication with said passageway.

6. The microstructure apparatus as recited in claim 5, further comprising: at least one chamber located on a second surface of said substrate that is opposite from said first surface, at least one fluidic compound that flows through said at least one passageway.

7. The microstructure apparatus as recited in claim 5, further comprising: a backing layer that is mounted onto a second surface of said substrate that is opposite from said first surface, wherein said backing layer is impregnated with at least one fluidic compound and thereby acts as a fluid reservoir for use with said substrate which contains at least one passageway and which allows said at least one fluidic compound to flow therethrough from said backing layer.

8. The microstructure apparatus as recited in claim 7, wherein both said substrate and backing layer are substantially flexible.

9. An apparatus according to claim 1, wherein said backing layer is impregnated with multiple actives in said at least one fluidic compound.

10. An apparatus according to claim 9, wherein at least one of said actives comprises a drug.

11. A microstructure apparatus according to claim 1, wherein said nonwoven absorbent backing layer is open to the atmosphere.

12. A microstructure apparatus according to claim 1, wherein said microelements comprise two or more different shapes.

13. A microstructure apparatus according to claim 12, wherein at least one microelement has a shape selected from the group consisting of a pyramid, an open topless box, a longitudinal wedge, a curved wedge, and an elongated triangle.

14. A microstructure apparatus according to claim 1, wherein the microelements are of two or more different sizes.

15. A microstructure apparatus according to claim 14, wherein said microelements are of two or more different shapes.

16. A microstructure apparatus according to claim 15, wherein at least one microelement has a shape selected from the group consisting of a pyramid, an open topless box, a longitudinal wedge, a curved wedge, and an elongated triangle.

* * * * *